US012171767B2

(12) United States Patent
Dugi et al.

(10) Patent No.: US 12,171,767 B2
(45) Date of Patent: Dec. 24, 2024

(54) USES OF DPP IV INHIBITORS

(71) Applicant: Boehringer Ingelheim International GmbH, Ingelheim am Rhein (DE)

(72) Inventors: Klaus Dugi, London (GB); Frank Himmelsbach, Mittelbiberach (DE); Michael Mark, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 228 days.

(21) Appl. No.: 17/681,997

(22) Filed: Feb. 28, 2022

(65) Prior Publication Data

US 2022/0184088 A1    Jun. 16, 2022

Related U.S. Application Data

(60) Division of application No. 16/829,610, filed on Mar. 25, 2020, now Pat. No. 11,291,668, which is a continuation of application No. 16/103,096, filed on Aug. 14, 2018, now abandoned, which is a division of application No. 15/372,702, filed on Dec. 8, 2016, now Pat. No. 10,080,754, which is a continuation of application No. 14/853,328, filed on Sep. 14, 2015, now abandoned, which is a continuation of application No. 14/161,007, filed on Jan. 22, 2014, now Pat. No. 9,173,859, which is a continuation of application No. 12/946,193, filed on Nov. 15, 2010, now Pat. No. 8,673,927, which is a continuation of application No. 11/744,703, filed on May 4, 2007, now Pat. No. 8,232,281.

(51) Int. Cl.

| A61K 31/522 | (2006.01) |
|---|---|
| A61K 31/155 | (2006.01) |
| A61K 31/197 | (2006.01) |
| A61K 31/4184 | (2006.01) |
| A61K 31/4985 | (2006.01) |
| A61K 31/5025 | (2006.01) |
| A61K 31/52 | (2006.01) |
| A61K 31/7048 | (2006.01) |
| A61K 45/06 | (2006.01) |

(52) U.S. Cl.
CPC .......... *A61K 31/522* (2013.01); *A61K 31/155* (2013.01); *A61K 31/197* (2013.01); *A61K 31/4184* (2013.01); *A61K 31/4985* (2013.01); *A61K 31/5025* (2013.01); *A61K 31/7048* (2013.01); *A61K 45/06* (2013.01); *A61K 31/52* (2013.01)

(58) Field of Classification Search
CPC .. A61K 31/522; A61K 31/155; A61K 31/197; A61K 31/4184; A61K 31/4985
See application file for complete search history.

(56) References Cited

U.S. PATENT DOCUMENTS

| 2,056,046 A | 9/1936 | Fourneau |
|---|---|---|
| 2,375,138 A | 5/1945 | Victors |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,159,345 A | 6/1979 | Takeo et al. |
| 4,382,091 A | 5/1983 | Benjamin et al. |
| 4,599,338 A | 7/1986 | Regnier et al. |
| 4,639,436 A | 1/1987 | Junge et al. |
| 4,687,777 A | 8/1987 | Meguro et al. |
| 4,743,450 A | 5/1988 | Harris et al. |
| 4,764,466 A | 8/1988 | Suyama et al. |
| 4,816,455 A | 3/1989 | Schickaneder et al. |
| 4,873,330 A | 10/1989 | Lindholm |
| 4,968,672 A | 11/1990 | Jacobson et al. |
| 5,034,225 A | 7/1991 | Bennett et al. |
| 5,041,448 A | 8/1991 | Janssens et al. |
| 5,051,509 A | 9/1991 | Nagano et al. |
| 5,051,517 A | 9/1991 | Findeisen et al. |

(Continued)

FOREIGN PATENT DOCUMENTS

| AU | 2003280680 A1 | 6/2004 |
|---|---|---|
| AU | 2009224546 A1 | 9/2009 |

(Continued)

OTHER PUBLICATIONS

National Program for Care Guidelines, "Type 2 Diabetes mellitus." 2002, First Edition, pp. 1-50.
Nationale Versorgungs-Leitlinie, Diabetes Mellitus, 2004.
Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Dlabetes Obesity and Metabolism, 2007, vol. 9, No. 2, pp. 194-205.
News Article, https:/www.in-phamratechnologist. com-Article-France-and-maerck-say-reformulated-Euthyrox-is-safe.)—Sep. 17, 2017, 1 page.

(Continued)

*Primary Examiner* — Kevin E Weddington
(74) *Attorney, Agent, or Firm* — David L. Kershner

(57) ABSTRACT

The specification describes the use of selected DPP IV inhibitors for the treatment of physiological functional disorders and for reducing the risk of the occurrence of such functional disorders in at-risk patient groups. In addition, the use of the above-mentioned DPP IV inhibitors in conjunction with other active substances is described, by means of which improved treatment outcomes can be achieved. These applications may be used to prepare corresponding medicaments.

19 Claims, No Drawings

(56) References Cited

U.S. PATENT DOCUMENTS

| | | |
|---|---|---|
| 5,084,460 A | 1/1992 | Munson, Jr. et al. |
| 5,120,712 A | 6/1992 | Habener |
| 5,130,244 A | 7/1992 | Nishimaki et al. |
| 5,164,526 A | 11/1992 | Macher |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,777,115 A | 7/1998 | Leigh et al. |
| 5,830,908 A | 11/1998 | Grunenberg et al. |
| 5,879,708 A | 3/1999 | Makino et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer et al. |
| 6,200,958 B1 | 3/2001 | Odaka et al. |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,399,101 B1 | 6/2002 | Frontanes et al. |
| 6,448,323 B1 | 9/2002 | Jordan et al. |
| 6,548,481 B1 | 4/2003 | Demuth et al. |
| 6,579,868 B1 | 6/2003 | Asano et al. |
| 6,689,353 B1 | 2/2004 | Wang et al. |
| 6,699,845 B2 | 3/2004 | Asahi |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,890,898 B2 | 5/2005 | Bachovchin et al. |
| 6,995,183 B2 | 2/2006 | Hamann et al. |
| 7,034,039 B2 | 4/2006 | Oi et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,220,750 B2 | 5/2007 | Himmelsbach et al. |
| 7,235,538 B2 | 6/2007 | Kanstrup et al. |
| 7,247,478 B2 | 7/2007 | Eberhardt et al. |
| 7,282,219 B2 | 10/2007 | Nomura et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,754,481 B2 | 7/2010 | Eberhardt et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 7,919,572 B2 | 4/2011 | Angot et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 * | 7/2012 | Dugi ................ A61K 31/4985 514/342 |
| 8,338,450 B2 | 12/2012 | Arora et al. |
| 8,455,435 B2 | 6/2013 | Franz et al. |
| 8,513,264 B2 | 8/2013 | Mark et al. |
| 8,541,450 B2 | 9/2013 | Pfrengle et al. |
| 8,637,530 B2 | 1/2014 | Pfrengle et al. |
| 8,664,232 B2 | 3/2014 | Himmelsbach et al. |
| 8,673,927 B2 * | 3/2014 | Dugi ................ A61K 31/5025 514/263.21 |
| 8,679,520 B2 | 3/2014 | Horres et al. |
| 8,697,868 B2 | 4/2014 | Himmelsbach et al. |
| 8,785,455 B2 | 7/2014 | Hotter et al. |
| 8,846,695 B2 | 9/2014 | Dugi |
| 8,853,156 B2 | 10/2014 | Dugi et al. |
| 8,865,729 B2 | 10/2014 | Sieger et al. |
| 8,883,800 B2 | 11/2014 | Pfrengle et al. |
| 8,883,805 B2 | 11/2014 | Pfrengle et al. |
| 8,962,636 B2 | 2/2015 | Pfrengle et al. |
| 9,034,883 B2 | 5/2015 | Klein et al. |
| 9,108,964 B2 | 8/2015 | Himmelsbach et al. |
| 9,149,478 B2 | 10/2015 | Klein et al. |
| 9,155,705 B2 | 10/2015 | Friedl et al. |
| 9,173,859 B2 * | 11/2015 | Dugi ....................... A61P 5/38 |
| 9,186,392 B2 | 11/2015 | Klein et al. |
| 9,199,998 B2 | 12/2015 | Pfrengle et al. |
| 9,212,183 B2 | 12/2015 | Sieger et al. |
| 9,266,888 B2 | 2/2016 | Sieger et al. |
| 9,321,791 B2 | 4/2016 | Himmelsbach et al. |
| 9,415,016 B2 | 8/2016 | Friedl et al. |
| 9,486,426 B2 | 8/2016 | Eller |
| 9,457,029 B2 | 10/2016 | Dugi et al. |
| 9,486,526 B2 | 11/2016 | Dugi |
| 9,493,462 B2 | 11/2016 | Sieger |
| 9,526,730 B2 | 12/2016 | Klein et al. |
| 9,815,837 B2 | 11/2017 | Sieger |
| 10,023,574 B2 | 7/2018 | Himmelsbach |
| 10,034,877 B2 | 7/2018 | Dugi |
| 10,092,571 B2 | 10/2018 | Dugi et al. |
| 10,155,000 B2 | 12/2018 | Meinicke et al. |
| 10,301,313 B2 | 5/2019 | Sieger et al. |
| 10,973,827 B2 | 4/2021 | Friedl et al. |
| 11,033,552 B2 | 6/2021 | Kohlrausch et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0042393 A1 | 4/2002 | Oobae et al. |
| 2002/0049164 A1 | 4/2002 | Demuth et al. |
| 2002/0115718 A1 | 8/2002 | Chen et al. |
| 2002/0137903 A1 | 9/2002 | Ellsworth et al. |
| 2002/0160047 A1 | 10/2002 | Hussain et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0040490 A1 | 2/2003 | Sugiyama et al. |
| 2003/0078269 A1 | 4/2003 | Pearson et al. |

(56) References Cited

U.S. PATENT DOCUMENTS

| | | |
|---|---|---|
| 2003/0100563 A1 | 5/2003 | Edmondson et al. |
| 2003/0104053 A1 | 6/2003 | Gusler et al. |
| 2003/0104983 A1 | 6/2003 | DeFelippis et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0153509 A1 | 8/2003 | Bachovchin et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0018468 A1 | 1/2004 | Gorokhovsky |
| 2004/0022866 A1 | 2/2004 | Rampoldi et al. |
| 2004/0023981 A1 | 2/2004 | Ren et al. |
| 2004/0034014 A1 | 2/2004 | Kanstrup et al. |
| 2004/0037883 A1 | 2/2004 | Zhou et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097399 A1 | 5/2004 | Rapin et al. |
| 2004/0097410 A1 | 5/2004 | Zheng et al. |
| 2004/0097510 A1 | 5/2004 | Himmelsbach et al. |
| 2004/0106655 A1 | 6/2004 | Kitajima et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0152659 A1 | 8/2004 | Matsuoka et al. |
| 2004/0152720 A1 | 8/2004 | Hartig et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259843 A1 | 12/2004 | Madar et al. |
| 2004/0259903 A1 | 12/2004 | Boehringer et al. |
| 2004/0266806 A1 | 12/2004 | Sanghvi et al. |
| 2005/0020484 A1 | 1/2005 | Harada et al. |
| 2005/0020574 A1 | 1/2005 | Hauel et al. |
| 2005/0026921 A1 | 2/2005 | Eckhardt et al. |
| 2005/0027012 A1 | 2/2005 | Kohlrausch |
| 2005/0031682 A1 | 2/2005 | Cucala Escoi et al. |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0070694 A1 | 3/2005 | Gelfanova et al. |
| 2005/0097798 A1 | 5/2005 | Evans et al. |
| 2005/0107730 A1 | 5/2005 | Doty et al. |
| 2005/0119162 A1 | 6/2005 | Harada et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0244502 A1 | 11/2005 | Mathias et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0263780 A1 | 12/2005 | Bour et al. |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0008829 A1 | 1/2006 | Hess |
| 2006/0034922 A1 | 2/2006 | Cheng et al. |
| 2006/0039968 A1 | 2/2006 | Manikandan et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0014855 A1 | 1/2007 | Rahul et al. |
| 2007/0027168 A1 | 2/2007 | Pfrengle et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0173452 A1 | 7/2007 | DiMarchi et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0197552 A1 | 8/2007 | Carr |
| 2007/0219178 A1 | 9/2007 | Muramoto |
| 2007/0254944 A1 | 11/2007 | Hughes |
| 2007/0259880 A1 | 11/2007 | Sakashita et al. |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0265349 A1 | 11/2007 | Rapin et al. |
| 2007/0281940 A1 | 12/2007 | Dugi et al. |
| 2007/0299076 A1 | 12/2007 | Piotrowski et al. |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0221200 A1 | 9/2008 | Allison et al. |
| 2008/0234291 A1 | 9/2008 | Francois et al. |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0054303 A1 | 2/2009 | Gougoutas et al. |
| 2009/0082256 A1 | 3/2009 | Abe et al. |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0253752 A1 | 10/2009 | Burkey et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2010/0317575 A1 | 12/2010 | Pinnetti et al. |
| 2010/0330177 A1 | 12/2010 | Pourkavoos |
| 2011/0009391 A1 | 1/2011 | Braun et al. |
| 2011/0028391 A1 | 2/2011 | Holst et al. |
| 2011/0046076 A1 | 2/2011 | Eickelmann et al. |
| 2011/0065731 A1 | 3/2011 | Dugi et al. |

(56) References Cited

U.S. PATENT DOCUMENTS

| | | |
|---|---|---|
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0206766 A1 | 8/2011 | Friedl et al. |
| 2011/0212982 A1 | 9/2011 | Christopher et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0064887 A1 | 3/2013 | Ito et al. |
| 2013/0122089 A1 | 5/2013 | Kohlrausch et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |
| 2013/0236543 A1 | 9/2013 | Ito et al. |
| 2013/0303462 A1 | 11/2013 | Klein |
| 2013/0303554 A1 | 11/2013 | Klein et al. |
| 2013/0315975 A1 | 11/2013 | Klein et al. |
| 2013/0317046 A1 | 11/2013 | Johansen |
| 2013/0324463 A1 | 12/2013 | Klein et al. |
| 2014/0100236 A1 | 4/2014 | Busl et al. |
| 2014/0274889 A1 | 9/2014 | Johansen et al. |
| 2014/0315832 A1 | 10/2014 | Broedl et al. |
| 2014/0343014 A1 | 11/2014 | Klein et al. |
| 2014/0371243 A1 | 12/2014 | Klein et al. |
| 2015/0196565 A1 | 7/2015 | Klein et al. |
| 2015/0246045 A1 | 9/2015 | Klein et al. |
| 2015/0265538 A1 | 9/2015 | Balthes et al. |
| 2016/0058769 A1 | 3/2016 | Graefe-Mody et al. |
| 2016/0082011 A1 | 3/2016 | Klein et al. |
| 2016/0089373 A1 | 3/2016 | Johansen et al. |
| 2016/0106677 A1 | 4/2016 | Boeck et al. |
| 2016/0310435 A1 | 10/2016 | Friedl et al. |
| 2017/0020868 A1 | 1/2017 | Dugi et al. |
| 2017/0354660 A1 | 12/2017 | Meinicke et al. |
| 2021/0205316 A1 | 7/2021 | Johansen et al. |
| 2021/0299120 A1 | 9/2021 | Gupta |
| 2022/0378797 A1 | 12/2022 | Friedl et al. |

FOREIGN PATENT DOCUMENTS

| | | |
|---|---|---|
| CA | 1123437 A1 | 5/1982 |
| CA | 2136288 A1 | 5/1995 |
| CA | 2375779 | 5/2000 |
| CA | 2418656 A1 | 2/2002 |
| CA | 2435730 A1 | 9/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2558446 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2599419 A1 | 11/2006 |
| CA | 2651019 A1 | 11/2007 |
| CA | 2651089 A1 | 11/2007 |
| CN | 101035522 A | 9/2007 |
| CN | 101234105 A | 8/2008 |
| CN | 101309689 A | 11/2008 |
| CN | 101590007 A | 12/2009 |
| CN | 104130258 A | 11/2014 |
| CN | 104418857 A | 3/2015 |
| CN | 105272982 A | 1/2016 |
| DE | 2205815 A1 | 8/1973 |
| DE | 2758025 A1 | 7/1979 |
| DE | 19705233 A1 | 8/1998 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0189941 A2 | 8/1986 |
| EP | 0223403 A2 | 5/1987 |
| EP | 0237608 A1 | 9/1987 |
| EP | 0248634 A2 | 12/1987 |
| EP | 0289282 A2 | 11/1988 |
| EP | 0342675 A2 | 11/1989 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0638567 A1 | 2/1995 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1310245 A1 | 5/2003 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1523994 A1 | 4/2005 |
| EP | 1535906 A1 | 6/2005 |
| EP | 1537880 A1 | 6/2005 |
| EP | 1557165 A1 | 7/2005 |
| EP | 1586571 A1 | 10/2005 |
| EP | 1604989 A1 | 12/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| EP | 2166007 A1 | 3/2010 |
| EP | 2308878 A2 | 4/2011 |
| EP | 3646859 A1 | 5/2020 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 61030567 | 2/1986 |
| JP | 770120 | 3/1995 |

(56) References Cited

FOREIGN PATENT DOCUMENTS

| | | |
|---|---|---|
| JP | 8333339 | 12/1996 |
| JP | 11193270 | 7/1999 |
| JP | 2000502684 A | 3/2000 |
| JP | 2001213770 A | 8/2001 |
| JP | 2001278812 A | 10/2001 |
| JP | 2001292388 A | 10/2001 |
| JP | 2002348279 A | 12/2002 |
| JP | 2003286287 A | 10/2003 |
| JP | 2003300977 A | 10/2003 |
| JP | 2003531118 A | 10/2003 |
| JP | 2004161749 A | 6/2004 |
| JP | 2004196824 A | 7/2004 |
| JP | 2004250336 A | 9/2004 |
| JP | 2006503013 A | 1/2006 |
| JP | 2006045156 A | 2/2006 |
| JP | 2006137678 A | 6/2006 |
| JP | 2007501231 A | 1/2007 |
| JP | 2007522251 A | 8/2007 |
| JP | 2007531780 A | 11/2007 |
| JP | 2008513390 A | 5/2008 |
| JP | 2008536881 A | 9/2008 |
| JP | 2010500326 A | 1/2010 |
| JP | 2010053576 A | 3/2010 |
| JP | 2010070576 A | 4/2010 |
| JP | 2010524580 A | 7/2010 |
| JP | 2010536734 A | 12/2010 |
| JP | 2011088838 A | 5/2011 |
| JP | 2011529945 A | 12/2011 |
| JP | 2012505859 A | 3/2012 |
| JP | 2005263780 | 3/2013 |
| KR | 20070111099 A | 11/2007 |
| WO | 8706941 A1 | 11/1987 |
| WO | 199107945 A1 | 6/1991 |
| WO | 199205175 A1 | 4/1992 |
| WO | 199219227 A2 | 11/1992 |
| WO | 199308259 A2 | 4/1993 |
| WO | 199402150 A1 | 2/1994 |
| WO | 199403456 A1 | 2/1994 |
| WO | 1994012200 | 6/1994 |
| WO | 9532178 A1 | 11/1995 |
| WO | 199609045 A1 | 3/1996 |
| WO | 199611917 A1 | 4/1996 |
| WO | 199636638 A1 | 11/1996 |
| WO | 199718814 A1 | 5/1997 |
| WO | 199723447 A1 | 7/1997 |
| WO | 199723473 A1 | 7/1997 |
| WO | 199728808 A1 | 8/1997 |
| WO | 199746526 A1 | 12/1997 |
| WO | 1998007725 | 2/1998 |
| WO | 199811893 | 3/1998 |
| WO | 9818770 A1 | 5/1998 |
| WO | 9819998 | 5/1998 |
| WO | 199822464 A1 | 5/1998 |
| WO | 199828007 A1 | 7/1998 |
| WO | 199840069 A2 | 9/1998 |
| WO | 1998046082 A1 | 10/1998 |
| WO | 199856406 A1 | 12/1998 |
| WO | 9903854 A1 | 1/1999 |
| WO | 199929695 A1 | 6/1999 |
| WO | 1999038501 A2 | 8/1999 |
| WO | 199950248 A1 | 10/1999 |
| WO | 1999049857 | 10/1999 |
| WO | 199956561 A1 | 11/1999 |
| WO | 199967279 A1 | 12/1999 |
| WO | 2000003735 A1 | 1/2000 |
| WO | 200012064 A1 | 3/2000 |
| WO | 200072873 | 5/2000 |
| WO | 200034216 A1 | 6/2000 |
| WO | 200034241 A1 | 6/2000 |
| WO | 0069464 A1 | 11/2000 |
| WO | 200066101 A2 | 11/2000 |
| WO | 0072799 A2 | 12/2000 |
| WO | 0078735 A1 | 12/2000 |
| WO | 200072973 A1 | 12/2000 |
| WO | 200073307 A2 | 12/2000 |
| WO | 200107441 A1 | 2/2001 |
| WO | 2001032158 A2 | 5/2001 |
| WO | 2001040180 A2 | 6/2001 |
| WO | 200152825 | 7/2001 |
| WO | 200152852 A1 | 7/2001 |
| WO | 2001047514 A1 | 7/2001 |
| WO | 2001051919 | 7/2001 |
| WO | 2001052825 A2 | 7/2001 |
| WO | 200168603 A2 | 9/2001 |
| WO | 2001066548 A1 | 9/2001 |
| WO | 2001068603 | 9/2001 |
| WO | 2001068646 A1 | 9/2001 |
| WO | 200177110 A1 | 10/2001 |
| WO | 2001072290 A2 | 10/2001 |
| WO | 200196301 A1 | 12/2001 |
| WO | 200197808 A1 | 12/2001 |
| WO | 200202560 A2 | 1/2002 |
| WO | 200214271 A1 | 2/2002 |
| WO | 200224698 A1 | 3/2002 |
| WO | 2002053516 A2 | 7/2002 |
| WO | 2002068420 A1 | 9/2002 |
| WO | 2003000241 A2 | 1/2003 |
| WO | 2003000250 | 1/2003 |
| WO | 2003002531 A2 | 1/2003 |
| WO | 2003002553 A2 | 1/2003 |
| WO | 2003004496 A1 | 1/2003 |
| WO | 2003004498 A1 | 1/2003 |
| WO | 2003006425 A2 | 1/2003 |
| WO | 2003024965 A2 | 3/2003 |
| WO | 2003033686 A2 | 4/2003 |
| WO | 03038123 A2 | 5/2003 |
| WO | 2003034944 A1 | 5/2003 |
| WO | 2003035177 A2 | 5/2003 |
| WO | 2003037327 A1 | 5/2003 |
| WO | 2003053929 A1 | 7/2003 |
| WO | 2003055881 A1 | 7/2003 |
| WO | 2003057200 A2 | 7/2003 |
| WO | 2003057245 A1 | 7/2003 |
| WO | 2003059327 | 7/2003 |
| WO | 2003061688 A1 | 7/2003 |
| WO | 2003064454 A1 | 8/2003 |
| WO | 2003074500 A2 | 9/2003 |
| WO | 2003088900 A2 | 10/2003 |
| WO | 2003094909 A2 | 11/2003 |
| WO | 2003099279 A1 | 12/2003 |
| WO | 2003099836 A1 | 12/2003 |
| WO | 2003104229 A1 | 12/2003 |
| WO | 2003106428 A1 | 12/2003 |
| WO | 2004002924 A1 | 1/2004 |
| WO | 2004011416 A1 | 2/2004 |
| WO | 2004016587 A1 | 2/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004037169 A2 | 5/2004 |
| WO | 2004041820 A1 | 5/2004 |
| WO | 2004043940 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A1 | 8/2004 |
| WO | 2004074246 A2 | 9/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004104216 A2 | 12/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007137 A2 | 1/2005 |

(56) References Cited

FOREIGN PATENT DOCUMENTS

| | | |
|---|---|---|
| WO | 2005007647 A1 | 1/2005 |
| WO | 2005007658 A2 | 1/2005 |
| WO | 2005012288 A1 | 2/2005 |
| WO | 2005016365 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005075410 A1 | 8/2005 |
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A1 | 10/2005 |
| WO | 2005107730 A2 | 11/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2005119526 A1 | 12/2005 |
| WO | 2006005613 A1 | 1/2006 |
| WO | 2006027204 A1 | 3/2006 |
| WO | 2006029577 A1 | 3/2006 |
| WO | 2006029769 A1 | 3/2006 |
| WO | 2006036664 A1 | 4/2006 |
| WO | 2006040625 A1 | 4/2006 |
| WO | 2006041976 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006078593 A2 | 7/2006 |
| WO | 2006083491 A2 | 8/2006 |
| WO | 2006116157 | 11/2006 |
| WO | 2006129785 A1 | 12/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 07035665 A1 | 3/2007 |
| WO | 2007033350 A1 | 3/2007 |
| WO | 2007035355 A2 | 3/2007 |
| WO | 2007035665 A1 | 3/2007 |
| WO | 2007038979 A1 | 4/2007 |
| WO | 2007041053 A2 | 4/2007 |
| WO | 2007050485 A2 | 5/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007136151 A1 | 11/2007 |
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2008005569 A2 | 1/2008 |
| WO | 2008005576 A1 | 1/2008 |
| WO | 2008017670 | 2/2008 |
| WO | 2008017670 A1 | 2/2008 |
| WO | 2008022267 A2 | 2/2008 |
| WO | 2008042408 A2 | 4/2008 |
| WO | 2008055870 A1 | 5/2008 |
| WO | 2008055940 A2 | 5/2008 |
| WO | 2008070692 A2 | 6/2008 |
| WO | 2008077639 A1 | 7/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008097180 A1 | 8/2008 |
| WO | 2008113000 A1 | 9/2008 |
| WO | 2008130998 A2 | 10/2008 |
| WO | 2008131149 A2 | 10/2008 |
| WO | 2008137435 A1 | 11/2008 |
| WO | 2008114800 A3 | 12/2008 |
| WO | 2009011451 A | 1/2009 |
| WO | 2009022007 | 2/2009 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009063072 A2 | 5/2009 |
| WO | 2009091082 A1 | 7/2009 |
| WO | 2009099734 A1 | 8/2009 |
| WO | 2009111200 A1 | 9/2009 |
| WO | 2009112691 A2 | 9/2009 |
| WO | 2009121945 A2 | 10/2009 |
| WO | 2009123992 A1 | 10/2009 |
| WO | 199967278 | 12/2009 |
| WO | 2009147125 A1 | 12/2009 |
| WO | 201092124 | 2/2010 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010126908 A1 | 11/2010 |
| WO | 2010140111 A1 | 12/2010 |
| WO | 2010147768 A1 | 12/2010 |
| WO | 2011011541 A1 | 1/2011 |
| WO | 2011039337 A1 | 4/2011 |
| WO | 2011039367 A2 | 4/2011 |
| WO | 2011064352 A1 | 6/2011 |
| WO | 2011109333 | 9/2011 |
| WO | 2011113947 A1 | 9/2011 |
| WO | 2011138380 A1 | 11/2011 |
| WO | 2011138421 A1 | 11/2011 |
| WO | 2011154496 A1 | 12/2011 |
| WO | 2011161161 A1 | 12/2011 |
| WO | 2011163206 A2 | 12/2011 |
| WO | 2002014271 | 1/2012 |
| WO | 2012031124 A2 | 3/2012 |
| WO | 2012039420 A1 | 3/2012 |
| WO | 2012065993 A1 | 5/2012 |
| WO | 2012088682 A1 | 7/2012 |
| WO | 2012089127 A1 | 7/2012 |
| WO | 2012106303 A1 | 8/2012 |
| WO | 2012120040 A1 | 9/2012 |
| WO | 2013098372 A1 | 7/2013 |
| WO | 2013103629 A1 | 7/2013 |
| WO | 2013131967 A1 | 9/2013 |
| WO | 2013171167 A1 | 11/2013 |
| WO | 2013174768 A1 | 11/2013 |
| WO | 2013179307 A2 | 12/2013 |
| WO | 2014029848 A1 | 2/2014 |
| WO | 2014140284 A1 | 9/2014 |
| WO | 2014170383 A1 | 10/2014 |
| WO | 20160089373 | 1/2017 |

(56) References Cited

FOREIGN PATENT DOCUMENTS

| WO | 2017047970 A1 | 3/2017 |
|---|---|---|
| WO | 2020016232 | 1/2020 |
| WO | 2020016232 A1 | 1/2020 |

OTHER PUBLICATIONS

Nielsen, L., "Incretin Mimetics and DPP-IV Inhibitors for the Treatment of Type 2 Diabetes." Drug Discovery Today, 2005, vol. 10, No. 10, pp. 703-710.
Nihon Ijinpo, Japan Medicinal Journal, 2001, No. 4032, p. 137.
Novartis AG, Investor Relations Release, "Galvus, a new oral treatment for type 2 diabetes, receives positive opinion recommending European Union approval." Securities and Exchange Commission, Form 6-K, 2007, pp. 1-4.
Nursten, The Mailard Reaction, Chemistry, Biochemistry, and Implications, Chapter 10, 2018, p. 1-8.
O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.
Office Action for U.S. Appl. No. 10/695,597 mailed May 2, 2008.
Okano, Renal Clearance, New General Pharmaceutics, Revised 3rd Edition, 1987p. 213-215.
Oz, Helieh S., "Methionine Deficiency and Hepatic Injury in a Dietary Steatohepatitis Model." Digestive Diseases and Sciences, 2008, vol. 53, No. 3, pp. 767-776.
Park, Stability evalustion test for linagliptin formulation , CKD formuation lab, 2018.
Patani George A. et al.: "Bioisoterism : A Rational Approach in Drug Design", Chemical Reviews, 1996, vol. 96, No. 8, pp. 3147-3176.
Pearson, E. R. et al., "Variation in TCF7L2 Influences Therapeutic Response to Sulfonylureas." Diabetes, 2007, vol. 56, pp. 2178-2182.
Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Pham, New Onset Diabetes Mellitus After Solid Organ Transplantation, Endocrinology and Metabolism Clinics of North America, 2007, p. 873-890.
Pharmaceutical Manufacturing and Storage (Concepts and Design, Inc.) 2009.
Pietruck, F. et al., "Rosiglitazone is a safe and effective treatment option of new-onset diabetes mellitus after renal transplantation." Transplant International, 2005, vol. 18, pp. 483-486.
Pilgaard, K. et al., "The T allele of rs7903146 TCF7L2 is associated with impaired insulinotropic action of incretin hormones, reduced 24 h profiles of plasma insulin and glucagon, and increased hepatic glucose production in young healthy men." Diabetologia, 2009, vol. 52, pp. 1298-1307.
Plummer, C.J.G. et al., "The Effect of Melting Point Distributions on DSC Melting Peaks." Polymer Bulletin, 1996, vol. 36, pp. 355-360.
Portincasa, Current Pharmacological Treatment of Nonalcoholic Fatty Liver, Current Medicinal Chem, 2006, p. 2889-2900.
Pospisilik, et al.; Dipeptidyl Peptidase IV Inhibitor Treatment Stimulates ?—Cell Survival and Islet Neogenesis in Streptozotocin-Induced Diabetic Rats; Diabetes, vol. 52, Mar. 2003 pp. 741-750.
Poudel, Resham R., "Latent autoimmune diabetes of adults: From oral hypoglycemic agents to early insulin." Indian Journal of Endocrinology and Metabolism, 2012, vol. 16, Supplement 1, pp. S41-S46.
Pradham, Wound-healing abnormalities in Diabetes, Dept. of surgertm Harvard, Touch Briefings, 2007.
Pratley, R. et al., "Inhibition of DPP-4: a new therapeutic approach for the treatment of type 2 diabetes." Current Medical Research and Opinion, 2007, vol. 23, No. 4, pp. 919-931.

Pregelatinized Starch, Drugs.com, derived from https://drugs.com/inactive/pregelatinized-starch-136.html, accessed Nov. 17, 2017.
Prescribing Information, Package insert for Leprinton tablets 100mg, Manufacturer: Tatsumi Kagaku Co., Ltd., Mar. 2003, pp. 1-3.
Press, Synthesis of 5,6 Dimethoxyquinazolin-2(1-H) ones, J. Heterocyclic Chwm, 1986.
Priimenko, B. A., et al.; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.
Publication Boehringer Ingelheim and Lilly's New type 2 Diabetes Treatment tradjenta, 2015, p. 1-7.
Rabinovitch, Thyophylline protects against diabetes in BB rats, Diabetologica, vol. 33, 1990.
Radermecker, Regis et al., "Lipodystrophy Reactions to Insulin." American Journal of Clinical Dermatology, 2007, vol. 8, pp. 21-28.
Rask-Madsen, C. et al., "Podocytes lose their footing." Nature, 2010, vol. 468, pp. 42-44.
Rhee et al.: "Nitrogen-15-Labeled Deoxynucleosides. 3. Synthesis of [3-15N]-2'-Deoxyadenosine" J. Am. Chem. Soc. 1990, 112, 8174-8175.
Rinsho-Yakuri, Jpn. J. Clin. Pharmacol. Ther. Pharmacokinetics: excretion, 30(3) 1999. 2 pages.
Rosenbloom, et al., "Type 2 Diabetes mellitus in the child and adolescent", Pediatric Diabetes, 2008, p. 512-526.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Rosenstock, J. et al., "Triple Therapy in Type 2 Diabetes." Diabetes Care, 2006, vol. 29, No. 3, pp. 554-559.
Rowe, R. et al., Handbook of Pharmaceutical Excipients, Fourth Edition, Pharmaceutical Press and American Pharmaceutical Association, 2003, pp. 323-332., 373-377, 609-611.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Salomon, J., et al; Ultraviolet and g-Ray-Induced Reactions of Nucleic Acid Constituents. Reactions of Purines with Amines; Photochemistry and Photobiology (1974) vol. 19 pp. 21-27.
Sampanis, Hippokratia, Management of Hyperglcemia in patients with diabetes mellitus and chronic renal failure, vol. 12, p. 22-27, 2008.
Sarafidis, P. et al., "Cardiometabolic Syndrome and Chronic Kidney Disease: What is the link?" JCMS 2006, 1: p. 58-65.
Sathananthan, A., et al., "Personalized pharmacotherapy for type 2 diabetes mellitus". Personalized Medicine 2009 Future Medicine Ltd, vol. 6, No. 4, Jul. 2009, p. 417-422.
Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.
Schafer, Impaired glucagen like peptide 1 induced insulin secretions in carriers of transcription, Diabetologica, vol. 50, 2007.
Scheen, Clinical Pharmacokinetics of metformin, Clinical Pharmacokinetics, vol. 30, No. 5, 1996, p. 359-371.
Horikawa, Synergistic Efffect of a-glucosidase inhibitors and dipeptidyl peptidase 4 inhibitor treatment, Journal of Diabetes Investigation, 2011, vol. 2, p. 200-203.
Horsford, E. N. "On the source of free hydrochloric acid in the gastric juice." Proceedings of the Royal Society of London, Published in 1868-1869, vol. 17, pp. 391-395.
Houben-Weyl, Oxygen Compounds, Methods of Organic Chemistry, 1929, 5 pages.
Hu, Diabetes Mellitus and Cardiovascular Disease, People's Military Medical Press, 2005, p. 211.

(56) References Cited

OTHER PUBLICATIONS

Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.
Huang, et al. Elimination of metformin-croscarmellose sodium interaction by competition, International Journal of Pharmaceutics, 2006, p. 33-39.
Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.
Huettner, Diabetes, Novel and Selective Xanthine, Jun. 2007 Supplement vol. 56.
Hull, R. et al., "Nephrotic syndrome in adults." British Medical Journal, 2008, vol. 336, pp. 1185-1190.
Hunziker, D. et al., "Inhibitors of DPP IV-recent advances and structural views", Current Topics in Medicinal Chemistry, 2005, vol. 5 issue 16, pp. 1623-1637.
Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.
Inagaki, Linagliptin provides effective, well-tolerated add-on therapy to pre-existing oral antidiabetic therapy over 1 year in Japanese patients with type 2 diabetes, Diabetes, Obesity and Metabolis, 2013, p. 833-843.
International Search Report—European Search Report for PCT/EP2003/09127 mailed Mar. 1, 2011.
International Search Report and Written Opinion for PCT/EP2006/064657 mailed Nov. 2, 2006.
International Search Report and Written Opinion for PCT/EP2007/054201 mailed Aug. 29, 2007.
International Search Report and Written Opinion for PCT/EP2007/054270 mailed Aug. 14, 2007.
International Search Report and Written Opinion for PCT/EP2008/060740 mailed Mar. 30, 2009.
International Search Report and Written Opinion for PCT/EP2009/053978 mailed Sep. 29, 2009.
International Search Report and Written Opinion for PCT/EP2009/056722 mailed Aug. 13, 2009.
International Search Report and Written Opinion for PCT/EP2009/060521 mailed Mar. 9, 2010.
International Search Report and Written Opinion for PCT/EP2009/063511 mailed Feb. 26, 2010.
International Search Report and Written Opinion for PCT/EP2009/067772 mailed Apr. 14, 2010.
International Search Report and Written Opinion for PCT/EP2010/050103 mailed Mar. 22, 2010.
International Search Report and Written Opinion for PCT/EP2010/051093 mailed Jul. 14, 2010.
International Search Report and Written Opinion for PCT/EP2010/051817 dated Jun. 8, 2010.
International Search Report and Written Opinion for PCT/EP2010/064691 mailed Apr. 6, 2011.
International Search Report and Written Opinion for PCT/EP2010068349 mailed Feb. 4, 2011.
International Search Report and Written Opinion for PCT/EP2011/054169 mailed Aug. 4, 2011.
International Search Report and Written Opinion for PCT/EP2011/057163 mailed Jun. 27, 2011.
International Search Report and Written Opinion for PCT/EP2011/057256 mailed Jul. 22, 2011.
International Search Report and Written Opinion for PCT/EP2011/060449 mailed Sep. 27, 2011.
International Search Report and Written Opinion for PCT/EP2011/070156 dated Jan. 17, 2012.
International Search Report and Written Opinion for PCT/EP2012/053910 mailed May 14, 2012.
International Search Report and Written Opinion for PCT/EP2012/063852 mailed Sep. 6, 2012.
International Search Report and Written Opinion for PCT/EP2012/077024 mailed Feb. 19, 2013.
International Search Report and Written Opinion for PCT/EP2013/054524 mailed on Apr. 24, 2013.
International Search Report and Written Opinion for PCT/EP2013/059828 mailed Aug. 6, 2013.
International Search Report and Written Opinion for PCT/EP2013/059831 mailed on Aug. 9, 2013.
International Search Report and Written Opinion for PCT/EP2013/060311 mailed Aug. 9, 2013.
International Search Report and Written Opinion for PCT/EP2013/060312 mailed on Sep. 4, 2013.
International Search Report and Written Opinion for PCT/EP2013/070978 mailed on Oct. 31, 2013.
International Search Report and Written Opinion for PCT/EP2014/055113 mailed May 16, 2014.
International Search Report and Written Opinion for PCT/EP2014/062398 mailed Aug. 20, 2014.
International Search Report and Written Opinion for PCT/EP2015/054114 mailed May 12, 2015.
International Search Report and Written Opinion for PCT/EP2015/074030 mailed Feb. 4, 2016.
International Search Report and Written Opinion for PCT/EP2017/064007, mailed Jun. 8, 2017.
International Search Report and Written Opinon for PCT/EP2007/054204 mailed Aug. 3, 2007.
International Search Report for PCT/EP03/12821 mailed Mar. 30, 2004.
International Search Report for PCT/EP03/13648 mailed Apr. 5, 2004.
International Search Report for PCT/EP2002/01820 mailed May 7, 2002.
Clinical Trials, NCT006002472, BI 1356 In combination with Metformin submitted Feb. 27, 2014.
Clinical Trials, No. NCT00309608, "Efficacy and Safety of BI 1356 BS in Combination with Metformin in Patients With type2 Diabetes" 2009, pp. 1-3.
Clinical Trials, No. NCT00622284, "Efficacy and Safety of BI 1356 in combination with metformin in patients with type 2 diabetes" 2012, pp. 1-5.
Clinical Trials. "View of NCT00601250 on Jan. 25, 2008: Efficacy and Safety of BI 1356 vs Placebo added to Metformin Background Therapy in Patients with Type 2 Diabetes" clinical trials. gov Archive, [Online] Jan. 25, 2008 URL:http://clinicaltrials.gov/archive/NCTO0601250/2008_01_25 [retrieved on Feb. 27, 2009].
Clinical Trials. NCTO0622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
Clinical Trials.gov, 52-week add-on to metformin comparison of saxagliptin and sulphonurea, NCT00575588, 2007.
Clinical Trials.gov, Efficacy and Safety of BI 1356 in Combination with Metformin in Patients with Type 2 Diabetes, NCT00309608, 2006.
Clinical Trials.gov, Efficacy and Safety of Lingliptin in Elderly Patients with Type 2 Diabetes, Mar. 10, 2010, NCT01084005.
Clinical Trials.gov, for BI1356 for Patients in Combination wtih Metormin in Patients with Type 2 Diabetes.2014.
Clinical Trials.gov, NCT00622284, Efficacy and Safety of BI 1356 in Combination with Metformin in Patients with Type 2 Diabetes, 2013.
Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.
Clinical Trials: NCT00103857, "A Multicenter, Randomized, Double-Blind Factorial Study of the Co-Administration of MK0431 and Metformin in Patients With Type 2 Diabetes Mellitus Who Have Inadequate Glycemic Control" last updated on Apr. 27, 2015.

(56) References Cited

OTHER PUBLICATIONS

Clinical Trials: NCT00309608, "Efficacy and Safety of BI 1356 BS (Linagliptin) in Combination With Metformin in Patients With type2 Diabetes" Boehringer Ingelheim Pharmaceuticals, last updated on Jun. 24, 2014.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.
Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.
Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.
Clinical Trials: NCT00798161. "Safety and efficacy of Bi 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.
Colorcon (retrieved from website http://www.colorcon.com/products-formulation/all-products/film-coatings/immediate-release/opadry, published2015).
Colorcon, "Lactose Replacement with Starch 1500 in a Direct Compression Formula." 2005, pp. 1-4.
Colorcon, "Reducing Coated Tablet Defects from Laboratory through Production Scale: Performance of Hypromellose or Polyvinyl Alcohol-Based Aqueous Film Coating Systems." Opadry II, 2009, pp. 1-7.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
Conarello, S.L. et al., "Mice lacking dipeptidyl peptidase IV are protected against obesity and insulin resistance". PNAS, May 27, 2003, vol. 100, No. 11, p. 6825-6830.
Connelly, Dipeptyl peptidase-4 inhibition improves left ventricular function in chronic kidney disease, Clinical and Investigative Medicine, vol. 37, 2014, p. 172-185.
Controlling Temperature (Guidelines for the Storage of Essential Medicines and Other Health Commodities, 2003, http://apps.who.int.medicinedocs/en/d/Js4885e/6.5html), 5 pages.
Cotton, M.L. et al., "L-649,923—The selection of an appropriate salt form and preparation of a stable oral formulation." International Journal of Pharmaceutics, 1994, vol. 109, Issue 3, pp. 237-249.
Craddy, P. et al., "Comparative Effectiveness of Dipeptidylpeptidase-4 Inhibitors in Type 2 Diabetes: A Systematic Review and Mixed Treatment Comparison." Diabetes Therapy, 2014, vol. 5, No. 1, pp. 1-41.
Crowe, E. et al., "Early identification and management of chronic kidney disease: summary of NICE guidance." British Medical Journal, 2008, vol. 337, pp. 812-815.
Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.
Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X, Nov. 1980, p. 1497-1500.
Dave, Rutesh H. "Overview of pharmaceutical excipients used in tablets and capsules." Drug Topics, Oct. 24, 2008.
Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.
Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.
Deacon, C.F., et al. Inhibitors of dipeptidyl peptidase IV: a novel approach for the prevention and treatment of Type 2 diabetes? Expert Opinion on Investigational Drugs, Sep. 2004, vol. 13, No. 9, p. 1091-1102.
Deacon, Carolyn F., "Dipeptidyl peptidase 4 inhibition with sitagliptin: a new therapy for Type 2 diabetes." Expert Opinion on Investigational Drugs, 2007, vol. 16, No. 4, pp. 533-545.
Definition of "prevent", e-dictionary, Aug. 15, 2013, http://dictionary.reference.com/browse/prevent.
Del Prato, Diabetes, Obesity and Metabolism, Effect of linagliptin monotherapy on glycemic control and markers of b-cell function in patients with inadequately controlled type 2 diabetes: a randomized controlled trial, 2011, p. 258-267.
DeMeester, I. et al.; "CD26, let it cut or cut it down", Review: Immunology Today; Aug. 1999, vol. 20, No. 8 pp. 367-375.
Demuth, H-U. et al., "Type 2 diabetes—Therapy with dipeptidyl peptidase IV inhibitors". Biochimica et Biophysica Acta, vol. 1751(1), 2005, p. 33-44.
Diabetes and Foot ulcers, www.diabetes.co.uk/diabetes-complications/diabetic-foot-ulcers.html, 2018.
Diabetes Frontier, 2007, vol. 18, No. 2, p. 145-148.
Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/tc/diabetic-retinopathy-prevention?print=true>.
Diabetes, Type 1 Diabetes-Associated Autoantibodies, 2009, vol. 52, Issue 8, p. 675-677.
Diabetesincontrol.com "EASD: Eucreas, a Combination of Galvus and Metformin, Recommended for Approval." Diabetes in Control.com, Sep. 25, 2007, Retrieved from internet on Nov. 30, 2012, http://www.diabetesincontrol.com/articles/53-diabetes-news/5145.
Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.
DiFeo, Drug Product Development, A Technical Review of Chemistry, Drug Development and Industrial Pharmacy, vol. 29, 2003, p. 939-958.
Doopedia, Maillard Reaction.
Drucker, Daniel J., "Dipeptidyl Peptidase-4 Inhibition and the Treatment of Type 2 Diabetes." Diabetes Care, 2007, vol. 30, No. 6, pp. 1335-1343.
Drucker, et al.., The incretin system: glucagon-like peptide-1 receptor agonists and dipeptidyl peptidase-4 inhibitors in type 2 diabetes. Lancet, 2006, 368: 1696-705.
Scheen, Efficacy and Safety of Jentadueto, Expert Opinion on Drug and Safety, vol. 12, No. 2, 2013, p. 275-289.
Schillinger, M. et al., "Restenosis after percutaneous angioplasty: the role of vascular inflammation." Vascular Health and Risk Management, 2005, vol. 1, No. 1, pp. 73-78.
Schmeider, Telmisartan in incipient and overt renal disease, J. Nephrol, vol. 24, 2011, 10 pages.
Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.
Schnapp, G. et al., "Analysis of binding kinetics and thermodynamics of DPPIV Inhibitors and their relationship to structure." International Workshop: The aspect of time in drug design, Schloss Rauischholzhausen, Marburg, Germany, Mar. 24-27, 2014.
Schnapp, G. et al., "Comparative Enzyme Kinetic Analysis of the Launched DPP-4 Inhibitors." American Diabetes Association, Abstract 1048-P, 2014.
Schurmann, C. et al., "The Dipeptidyl Peptidase-4 Inhibitor Linagliptin Attenuates Inflammation and Accelerates Epithelialization in Wounds of Diabetic ob/ob Mice." The Journal of Pharmacology and Experimental Therapeutics, 2012, vol. 342, No. 1, pp. 71-80.
Schwartz, M. S. et al., "Type 2 Diabetes Mellitus in Childhood: Obesity and Insulin Resistance". JAOA Review Article, vol. 108, No. 9, Sep. 2008, p. 518.
Scientific Discussion for Sifrol, European Public Assessment Reports, 2005, p. 1.

(56) References Cited

OTHER PUBLICATIONS

Scientific Discussion on Sifrol, EMEA, 2005, p. 1-9.
Scientific Discussion, EMEA, Pramipexole, 2005, pp. 1-10.
Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).
Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.
Seijin-byou, The Journal of Adult Diseases, 2008, vol. 38, p. 438-444., abstract attached.
Seino, Alogliptin plus voglibose in Japanese patients with type 2 diabetes: a randomized, double blind, placebo-controlled trial with an open label, long term extension, Current Medical Research and Opinion, 2011, vol. 27, p. 21-29.
Shanks, N. et al., Are animal models predictive for humans?, PEHM, Philosophy, Ethics, and Humanaities in Medicine, 4(2), 2009, 1-20.
Sharkovska, Y., et al., "DPP-4 Inhibition with Linagliptin Delays the Progression of Diabetic Nephropathy in db/db Mice." 48th EASD Annual Meeting, Berlin, Abstract 35, Oct. 2012.
Sheperd, Todd M. et al., "Efective management of obesity." The Journal of Family Practice, 2003, vol. 52, No. 1, pp. 34-42.
Shigai, "How to use medicines in case of kidney injury caused by medicine" Journal of the Japanese Association of Rural Medicine, vol. 51, 2002, p. 63-67.
Shintani, Maki, et al., "Insulin Resistance and Genes" Circulatory Sciences (1997) vol. 17, No. 12 pp. 1186-1188.
Shu, L. et al., "Decreased TCF7L2 protein levels in type 2 diabetes mellitus correlate with downregulation of GIP- and GLP-1 receptors and impaired beta-cell function." Human Molecular Genetics, 2009, vol. 18, No. 13, pp. 2388-2399.
Shu, L. et al., "Transcription Factor 7-Like 2 Regulates B-Cell Survival and Function in Human Pancreatic Islets." Diabetes, 2008, vol. 57, pp. 645-653.
Silverman, G. et al., "Handbook of Grignard Reagents." 1996, Retrieved online: <http://books.google.com/books?id=82CaxfY-uNkC&printsec=frontcover&dq=intitle:Handbook+intitle:of+intitle:Grignard+intitle:Reagents&hl=en&sa=X&ei=g06GU5SdOKngsATphYCgCg&ved=0CDYQ6AEwAA#v=onepage&q&f=false>.
Singhal, D. et al., "Drug polymorphism and dosage form design: a practical perspective." Advanced Drug Delivery Reviews, 2004, vol. 56, pp. 335-347.
Slotta, On Biguanides, Chem. Institute at the Univ. of Wroclaw, vol. 62, 1929.
Smithies, The Jackson Lab, Mouse Strain Datasheet, 2019, p. 1-2.
Sortino, M.A. et al., "Linagliptin: a thorough characterization beyond its clinical efficacy." Frontiers in Endocrinology, 2013, vol. 4, Article 16, pp. 1-9.
St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.
Stahl, Handbook of Pharmaceutical Salts, Properties, Selection and Use, 2002.
Stahl, P.H., "Handbook of Pharmaceutical Salts" C.G. Wermuth, Wiley-VCH, 2002, pp. 1-374.
Standl, E. et al., "Diabetes and the Heart." Diabetes Guidelines (DDG), 2002, pp. 1-25.
Stedman's Medical Dictionary, 27th edition, Def. of nephropathy, 1999, 1 page.
Sulkin, T.V. et al., "Contraindications to Metformin Therapy in Patients With NIDDM." Diabetes Care, 1997, vol. 20, No. 6, pp. 925-928.
Sune Negre, J. M. "New Galenic Contributions to Administration Forms". Continued Training for Hospital Pharmacists 3.2., (Publication date unavailable), Retrieved from internet on Feb. 23, 2011, http://www.ub.es/legmh/capitols/sunyenegre.pdf.
Susman,Ada: Linagliptin Works in Diabetic Kidney Disease, Med Page Today, 2011, 2 pages.
Suzuki, Y. et al., "Carbon-Carbon Bond Cleavage of a-Hydroxybenzylheteroarenes Catalyzed by Cyanide Ion: Retro-Benzoin Condensation Affords Ketones and Heteroarenes and Benzyl Migration Affords Benzylheteroarenes and Arenecarbaldehydes." Chemical Pharmaceutical Bulletin, 1998, vol. 46(2), pp. 199-206.
Tadayyon, M. et al., "Insulin sensitisation in the treatment of Type 2 diabetes." Expert Opinion Investigative Drugs, 2003, vol. 12, No. 3, pp. 307-324.
Takai, S. et al., "Significance of Vascular Dipeptidyl Peptidase-4 Inhibition on Vascular Protection in Zucker Diabetic Fatty Rats." Journal of Pharmacological Sciences, 2014, vol. 125, pp. 386-393.
Takeda Press Release: "Voglibose (BASEN) for the prevention of type 2 diabetes mellitus: A Randomized, Double-blind Trial in Japanese Subjects with Impaired Glucose Tolerance." 2008, Retrieved online Jul. 6, 2015. https://www.takeda.com/news/2008/20080526_3621.html.
Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.
Tanaka, S., et al.; "Suppression of Arthritis by the Inhibitors of Dipeptidyl Peptidase IV," In. J. Immunopharmac., vol. 19, No. 1, pp. 15-24, 1997.
Tang, Protection of DPP-4 inhibitors on cardiovascular, Drug Evaluation, vol. 9, 2012, p. 6-9.
Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.
Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.
The Textbook of Pharmaceutics, Pharmaceutical Subcommitee Hanrimwon, 2005, p. 1-6.
The textbooks of Pharmaceutics, Department of Pharmacy, Pharmaceutical Committee, 1996.
The Textbooks of Pharmaceutics, Department of Pharmacy, Pharmaceutical Subcommitee, 2000.
Third Party Observation for application No. EP20070728655, May 13, 2013.
Thomas, (R)-8-Amino-piperidin-1-yl)-7-but-2-ynyl-3-methyl-1-(4-methyl-quinazolin-2-ylmethyl)-3,7-dihydro-purine-2,6-dione(BI1236, a Novel Xanthine based Dipeptidyl Peptidase 4 inhibitor, has a Superior Potency and longer duration of action compared with other dipeptyl Peptidase-4 inhibitors, The Journal of Pharmacology and Experimental Therapeutica, vol. 325, 2008, p. 175-182.
Thomas, L. et al., "BI 1356, a novel and selective xanthine beased DPP-IV inhibitor, exhibits a superior profile when compared to sitagliptin and vildagliptin." Diabetologia, 2007, vol. 50, No. Suppl. 1, p. S363.
Knowler, W.C. et al., "Reduction in the Incidence of Type 2 Diabetes with Lifestyle Intervention or Metformin." The New England Journal of Medicine, 2002, vol. 346, No. 6, pp. 393-403.
Komori, Kiyoshi., "Treatment of Diabetes in Patients for Whom Metforming Treatment is Not Appropriate" Modern Physician (2008) vol. 28, No. 2 pp. 163-165.
Konstantinou, D. M. et al., "Pathophysiology-based novel pharmacotherapy for heart failure with preserved ejection fraction." Pharmacology & Therapeutics, 2013, vol. 140, No. 2, pp. 156-166.
Korom, S. et al; Inhibition of CD26/dipeptidyl peptidase IV activity in vivo prolongs cardiac allograft survival in rat recipients 1,2, Transplantation, May 27, 1997, vol. 63, No. 10, pp. 1495-1500.
Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.

(56) References Cited

OTHER PUBLICATIONS

Kumar, V. et al., "Maillard Reaction and Drug Stability." Maillard Reactions in Chemistry, Food, and Health, 1994, No. 151, pp. 20-27.

Kuno, Y. et al., "Effect of the type of lubricant on the characteristics of orally disintegrating tablets manufactured using the phase transition of sugar alcohol." European Journal of Pharmaceutics and Biopharmaceutics, 2008, vol. 69, pp. 986-992.

Kurozumi, Efficacy of a-glucosidase inhibitors combined with dipeptyl-peptidase-4 inhibitor for glucose fluctuation in patients with type 2 diabetes mellitus by continuous glucose monitoring, Journal of Diabetes Investigation, 2013, vol. 4, p. 393-398.

Lachman, L. et al., "The Theory and Practice of Industrial Pharmacy." Varghese Publishing House, Third Edition, 1987, pp. 190-194.

Lakatos, P. L. et al., "Elevated serum dipeptidyl peptidase IV (CD26, EC 3.4.14.5) activity in patients with primary biliary cirrhosis." Journal of Hepatol, 1999, vol. 30, p. 740.

Lakey, Technical Aspects of Islet Preparation, Translp, Int.m 2003, vol. 16, p. 613-632.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.

Lee Jones, K. et al., "Effect of Metformin in Pediatric Patients With Type 2 Diabetes." Diabetes Care, 2002, vol. 25, No. 1, pp. 89-94.

Leibovitz, E. et al., "Sitagliptin pretreatment in diabetes patients presenting with acute coronary syndrome: results from the Acute Coronary Syndrome Israeli Survey (ACSIS)." Cardiovascular Diabetology, 2013, vol. 12, No. 1, pp. 1-7.

Levien, T.L. et al, "New drugs in development for the treatment of diabetes", Diabetes Spectrum, American Diabetes Association, US, vol. 22, No. 2, Jan. 1, 2009, pp. 92-106.

Lieberman, H. et al., "Pharmaceutical Dosage Forms." Marcel Dekker, Inc., 1980, vol. 1, p. 38.

Lim, S. et al., "Effect of a Dipeptidyl Peptidase-IV Inhibitor, Des-Fluoro-Sitagliptin, on Neointimal Formation after Balloon Injury in Rats." Plos One, 2012, vol. 7, No. 4, pp. 1-11.

Linagliptin Monograph, Published by VACO PBM-SHG US Veteran's Administration, 2011, pp. 1-17.

Linagliptin, Pub Chem, Clinical Trial Search of Japan, https;//pubchem.ncbi.nlm.nih.gov/compound/10096344 dated Jun. 25, 2020.

Lindsay, J.R. et al., "Inhibition of dipeptidyl peptidase IV activity by oral metformin in Type 2 diabetes." Diabetic Medicine, 2005, vol. 22, pp. 654-657.

Lovshin, J.A. et al., "Incretin-based therapies for type 2 diabetes mellitus." Nature Reviews Endocrinology, 2009, vol. 5, pp. 262-269.

Luo, Shanghai Scientific and Technical Lit Publishing House, Theory and Practice of Modern Physical Pharmacy, vol. 4, 2005, p. 294.

Luo, Theory and Practice of Modern Physical Pharmacy, Shangai Scientific and Technical Literature Publishing House, 2005, p. 294.

Lyssenko, V. et al., "Mechanisms by which common variants in the TCF7L2 gene increase risk of type 2 diabetes." The Journal of Clinical Investigation, 2007, vol. 117, No. 8, pp. 2155-2163.

March, J. "Advanced Organic Chemistry: Reactions, Mechanisms, and Structure". Fourth Edition, 1992, pp. 652-653.

Mathieu, C. et al., "Antihyperglycaemic therapy in elderly patients with type 2 diabetes: potential tole of incretin mimetics and DPP-4 inhibitors." International Journal of Clinical Practice, 2007, vol. 61, Suppl. 154, pp. 29-37.

Matsumiya, Teruhiko, et al., "Therapeutic Drugs for Clinicians" Diagnosis and Treatment (2008) vol. 96, No. 2 pp. 389-390.

Matsuyama, Glucagen like peptide: a ptotent glucagonostatic hormone, Diabetes Research, 1988, p. 281-288.

Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.

McNay, David E.G. et al., "High fat diet causes rebound weight gain." Molecular Metabolism, 2013, vol. 2, pp. 103-108.

Medicine Department of Pharmacy, Pharmaceutical Subcommitte, Book Publishing Harwinton, 1996, p. 283.

Medline Plus, "Obesity" 2013, Retrieved from internet on Aug. 22, 2013, http://www.nlm.nih.gov/medlineplus/obesity.html.

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.

Mendes, F.D, et al. "Recent advances in the treatment of non-alcoholic fatty liver disease". Expert Opinion on Investigational Drugs, vol. 14, No. 1, Jan. 1, 2005, p. 29-35.

Merck Manual of Diagnosis and Therapy: "Obesity." 1999, 17th Edition, Chapter 5, pp. 58-62.

Merck manual, 18th Edition, published Apr. 25, 2007, p. 594-598, Japanese Edition.

Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.

Methocel Cellulose Ethers in Aqueous Systems for tablet coating: retrieved from Internet: http;//msdssearch.dow.com/PublishedLiteratureDOWCOM/dh_004a/0901b8038004ab56.pdf?filepath=198-00755.pd?fromPage=GetDoc, published2002. Retrieved Dec. 8, 2017, 3 pages.

Mettler Toledo "interpreting DSC curves Part 1: Dynamic Measurements" Jan. 2000. Available from www.masointechnology.ie.x/Usercom_11.pdf, 28 pages.

Mikhail, Investigating Drugs, Incretin Mimetics and dipeptidyl peptidase 4 inhibitors in clinical trials for the treatment of Type 2 diabetes, vol. 17, 2008, p. 845-853.

Mikhail, Nasser, "Incretin mimetics and dipeptidyl peptidase 4 inhibitors in clinical trials for the treatment of type 2 diabetes." Expert Opinion on Investigational Drugs, 2008, vol. 17, No. 6, pp. 845-853.

MIMS Jan. 2009, "Sitagliptin." pp. 152-153.

Mojsov, Insulintropin: Glucagin like peptide: Lab of Molecular Endocrinology, vol. 79, 1987, p. 616-619.

Morhenn, "Keratinacyte proliferation n wound healing and skin diseases", Immunology Today, vol. 9, Issue 4, 1988, p. 104.

Moritoh, Y. et al., "Combination treatment with alogliptin and voglibose increases active GLP-1 circulation, prevents the development of diabetes and preserves pancreatic beta-cells in prediabetic db/db mice." Diabetes, Obesity and Metabolism, 2010, vol. 12, pp. 224-233.

Nabors, Lyn O'Brien "Alternative Sweeteners." Marcel Dekker, Inc., 2001, pp. 235, 339-340.

Nachaegari, Coprocessed Excipients for Solid Dosage Forms, Pharmaceutical technology, 2004, 8 pages.

Naik, R. et al., "Latent Autoimmune Diabetes in Adults." The Journal of Clinical Endocrinology and Metabolism, 2009, vol. 94, No. 12, pp. 4635-4644.

Nar, Herbert "Analysis of Binding Kinetics and Thermodynamics of DPP-4 Inhibitors and their Relationship to Structure." 2nd NovAliX Conference: Biophysics in drug discovery, Strasbourg, France, Jun. 9-12, 2015.

Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.

International Search Report for PCT/EP2003/12821 mailed Mar. 30, 2004.

International Search Report for PCT/EP2003/13648 mailed Apr. 5, 2004.

International Search Report for PCT/EP2005/001427 mailed May 23, 2005.

International Search Report for PCT/EP2005/055711 dated Mar. 29, 2006.

International Search Report for PCT/EP2007/054204 mailed Mar. 8, 2007.

International Search Report for PCT/EP2007/058181 mailed Nov. 28, 2007.

(56) References Cited

OTHER PUBLICATIONS

International Search Report for PCT/EP2008/060738 mailed Nov. 5, 2008.
International Search Report for PCT/EP2009/060170 mailed Oct. 28, 2009.
International Search Report for PCT/EP2010/064691 mailed Jan. 20, 2011.
International Search Report for PCT/EP2013/060309 mailed Aug. 9, 2013.
International Search Report for PCT/EP2013/070979 mailed Nov. 26, 2013.
International Search Report for PCT/EP2014/060160 mailed Nov. 8, 2014.
International Search report for PCT/EP2019/069126, mailed Oct. 2, 2019.
International Search Report for PCT/EP2019/069131 mailed Oct. 8, 2019.
International Search Report for PCT/EP2019/EP069131 mailed Jan. 28, 2021.
Inukai, T., "Treatment of Diabetes in Patients for Whom Metformin Treatment is Not Appropriate." Modern Physician, 2008, vol. 28, No. 2, pp. 163-165.
Inzucchi, Silvio E., "Oral Antihyperglycemic Therapy for Type 2 Diabetes." The Journal of the American Medical Association, 2002, vol. 287, No. 3, pp. 360-372.
Isoda, Certificate of experimental Results, Analytical Research Development, 2021.
Isomaa, B. et al., "Cardiovascular Morbidity and Mortality Associated With the Metabolic Syndrome." Diabetes Care, 2001, vol. 24, No. 4, pp. 683-689.
Isomaa, Chronic Comlications in patients with slowly progressing atutoimmune type 1 diabetes, Diabetes Care, vol. 22, 1999, p. 1347-1353.
Iwamoto, Yasuhiko, "Insulin Glargine." Nippon Rinsho, 2002, vol. 60, Suppl. 9, pp. 503-515.
Janumet dosing instructions, Highlights of Prescribing information, 2008.
Janumet Prescribing Information, revised Jan. 2008.
Januvia Prescribing Information and Product Label, 2006.
Januvia, 25mg, 50mg, 100 mg, Summary of Product Characteristics, 2015, www.medicines.org.uk/EMC <http://www.medicines.org.uk/EMC>.
Jibiinkoka-Tenbo, Vision of Otorhinolaryngology, How to use antimicrobial drug in a patient with impairment of renal function, vol. 44, No. 3, 2001, p. 217-220.
Johansen, Cardiovascular safety with linagliptin on patients with type 2 diabetes mellitus, Cardiovascular Diabetology, 2012, vol. 11, p. 1-10.
Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 3, pp. 1-10.
Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.
John Hopkins Children's Center, "Liver Disorders and Diseases." Retrieved online May 26, 2014 <http://www.hopkinschildrens.org/non-alcoholic-fatty-liver-disease.aspx>.
Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.
Kanada, S. et al., "Safety, tolerability, pharmacokenetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA, Jun. 6-10, 2008.
Karaliede et al, Diabetes Care, Endothelial Factors and Diabetic Nephropathy, 2011, 34, Suppl 2, p. 291-296.
Kaur, Development of new incretin drugs: Promising Therapies, Indian Journal Pharmacology, 2006, vol. 38, Issue 2, p. 100-106.
Kawamori, Linagliptin monotherapy provides superior glycaemic control v. placebo or voglibose with comparable safety in Japanese patients with type 2 diabetes, a randomized , placebo and active comparator—controlled doiuble blind study, 2011, Diabetes, Obesity and Metabolism, p. 348-357.
Kelly. T., "Fibroblast activation protein-cx and dipeptidyl peptidase IV (CD26)P: Cell-surface proteases that activate cell signaling and are potential targets for cancer therapy". Drug Resistence Update 8, 2005, vol. 8. No. 1-2, pp. 51-58.
Kendall, D. M. et al., "Incretin Mimetics and Dipeptidyl Peptidase-IV Inhibitors: A Review of Emerging Therapies for Type 2 Diabetes." Diabetes Technology & Therapeutics, 2006, vol. 8, No. 3, pp. 385-398.
Kharkevich, D. A., "Educational Literature" Pharmacology (1987) Third Edition, Meditsina Press, Moscow pp. 47-48.
Kibbe, A., Editor. Handbook of Pharmaceutical Excipients, Third Edition, Copovidon—pp. 196-197, Date of Revision: Dec. 16, 2008. Mannitol—pp. 424-425, Date of Revision: Feb. 19, 2009, Published in 2009.
Kibbe, Handbook of Pharmaceutical Excipients, 3rd Edition, 2009, p. 104-107.
Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.
Kim, Comparison of DPP-4 Inhibitors, The Journal of Korean Diabetes, http:dx.doi.org/10.4093/jkd.2013.14.3.111. 6 pages.
Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.
Kim, Kwang-Rok et al., "KR-62436, 6-{2-{2-(5-cyano4,5-dihydropyrazol-1-yl)-2-oxoethylamino}ethylamino} nicotinonitrile, is a novel dipeptidyl peptidase-IV (DDP-IV inhibitor with anti-hyperglycemic activity" European Journal of Pharmacology 518, 2005, p. 63-70.
Kiraly, K. et al., "The dipeptidyl peptidase IV (CD26, EC 3.4.14.5) inhibitor vildagliptin is a potent antihyperalgesic in rats by promoting endomorphin-2 generation in the spinal cord." European Journal of Pharmacology, 2011, vol. 650, pp. 195-199.
Kirpichnikov, D. et al., "Metformin: An Update." Annals of Internal Medicine, 2002, vol. 137, No. 1, pp. 25-33.
Kishore, Preeti MD., "Complications of Diabetes Mellitus." Merck Manual Consumer Version, 2016, pp. 1-7.
Kleeman, Pharmaceutical Substances, Synthesesm Patents, Applications, p. 1196-1197, 1999.
Klein, T. et al., "Linagliptin alleviates hepatic steatosis and inflammation in a mouse model of non-alcoholic steatohepatitis." Medical Molecular Morphology, 2014, vol. 47, pp. 137-149.
Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.
Arenson, Neuropathy, Aniopathy, and sepsis in the diabetic foot, J. of american Podiatry assoc., vol. 72, 1982, p. 35-40.
Andrades, Bench to bedside review, Sepsis, from the redox point of view, Clinical care, vol. 15, 2011, 8 pages.
Holt, Textbook of Diabetes, 4th Ed., 2010, 48 pages.
Lee, Recent advances in the treatment of diabetes mellitus, Korean J. of Medicine, vol. 57, 1999, p. 836-848.
The Japan Diabetes Society, Practice Guidelines of Diabetes based on Scientific basis, May 25, 2004, p. 5-19, p. 37-56, p. 67-80, p. 93-121, p. 131-153.
Toshiaki, ABC18 for new diagnostics and treatments, The medical frontline, 2004, p. 106-112.

(56) References Cited

OTHER PUBLICATIONS

The Japan Diabetes Society, Guidelines for treatment of Diabetes, Feb. 14, 2006, p. 21-33, 41-55, 62-76.
Yamaguchi, Today's Therapeutic Guidelines, 2006, p. 518-520.
Sakura, Trends in development on oral diabetic agents and new developments of treatment, Clinical Endocrinology, vol. 3, 2011, p. 51-55.
Yoshimoto, Structure of DPP-4 and Antidiabetic Therapeutic Agents, Current Diabetology, vol. 3, p. 51-55.
Kawamori, Investigation of Diabetes, Soten Lmtd., 2004, p. 15-19.
Shigeta, MR Training Manual, Elsevier, 2004, p. 44-54, p. 67-74.
Ono, Diabetes and islet tranplantation, Japanese J. of clinical Pathology, vol. 54, 2006, p. 379-385.
Suzuki, Prospects of ISlet transplantation, Pharma medica, vol. 24, 2006, p. 67-71.
Shimada, MR Training Manual, Cardiovascular System, Elsevier, 2003, p. 2-58.
Kazunaga, Guidelines for Required dose Response, Pharmaceutical Examination, 1994, 1 page.
Ministry of Health, Clinical Pharmacokinetics Examination of Druge, vol. 796, 2001, 1 page.
Uematsu, Text of clinical Pharmacology, Nancodo, 1997, p. 45-51.
National Library of Medicine, Searching result of information for Clinical Trial NCT00309608 for Linagliptin from Clinicaltrials.gov, Mar. 31, 2006.
Boehringer Ingelheim Japan, Interview Form for Trazenta Tablets 5 mg, Apr. 2022, 18 version.
Katakami, Action and usage of oral hypoglycemic agents, Clinica, vol. 31, 2004, p. 398-399.
Sanwa Kagaku Kenkyusho, Package Insert fo Seibule tablets 25mg, 50 mg, 75mg, Aug. 2021.
Funabashi, Basic concept for metabolic syndrome, Pharma medica, vol. 22, 2004, p. 11-16, 21-24.
Kita, Satin based anti-arteriosclerotic drugs, vol. 32, 2000, p. 932-936.
Viatris Pharmaceuticals, Package Insert for Lipitor, 10mg. Nov. 2022.
Sun Pharma Japan Limited, Package insert for Lopresor Tablet, 20mg, 40mg, Oct. 2021.
Sumitomo Pharma Co., Package insert for AmlodinTablets, 2.5mg, 5mg, 10mg, and Amlodin MD Tablets, 2.5mg, 5mg, 10mg, Dec. 2022.
Pfizer Lab Division, Inc., Drug Label for ALTACE Ramipril Casules, Feb. 2022.
Novartis Pharma, K.K. Package Insert for Diovan Tablets, 20mg, 40mg, 80mg, 16omg, Apr. 2020.
Boehringer Ingelheim Japan, Package insert for Micardis Tablets, 20mg, 40mg, 80mg, Jul. 2020.
Viatros Pharmaceuticals, Co., Ltd., Interview form for Lipitor Tablets, 5mg, 10mg, Dec. 2022.
Hotchkiss, The pathophysiology and Treatment of Sepsis, The New England J. of Medicine, vol. 348, 2003, 13 pages.
Russell, Treatment of Sepsis, New England J. of Medicine, vol. 355, 2006, 15 pages.
Dedov, Russian Federation Ministry of Health, Sugar Glabetes, 8th edition, vol. 20, 2017, 22 pages.
Graefe-Mody, The novel DPP-4 inhibitor BI 1356 (proposed tradename ONDERO) and metformin can be safely co-administered, Abstract, Diabetes, online, 2008, retrieved from internet, URL: http://professional.diabetes.org/Content/posters/2008/p553-P.pdf>retrieved on Dec. 21, 2009.
Wang, BI-1356, dipeptyl-peptidase IV inhibitor, antidiabetic agent, Drugs of the future, Prous science, vol. 33, No. 6, 2008, p. 473-477.
Pei, From the bench to the bedside, dipeptidyl peptidase IV inhibitors, a new class of oral antihyperglycemic agents, Current Opinion in drug discovery and development, vol. 11, 2008, p. 512-532.
Nathan, Management of hypoglycemia in type 2 diabetes, Diabetes care, vol. 29, 2006, 10 pages.
Ristic, Improved glycemic contol with dipeptyl peptidase 4 inhibitionin patients with type 2 diabetes, Diabetes, Obesity and metabolism, vol. 7, 2005, 8 pages.
Maedler, Sulfonylurea Induced b-cell Apoptosis in Clutured Human islets, The j. of Clinical Endocrinology & Metabolism, vol. 1, 2005, 6 pages.
Kendall, Effects of Exenatide on Glycemic control over 30 weeks in patients with type 2 diabetes treated with metformin and a Sulfonylurea, Diabetes Care, vol. 28, 2005, 9 pages.
Meneilly, Diabetes in Elderly adults, J. of Gerontology, vol. 56A, 2001, 9 pages.
Herrington, Metformin: effective and safe in renal disease?, Int. Urol. Nephrol., vol. 10, 2008, 7 pages.
Ashford, Bioavailability-physiochemical and dosage form factors, Aulton's Pharmaceutics, 3rd Edition, 2007, p. 286-289.
Yu, Evalution of USP Apparatus 3 Dissolution Testing of Immediate Release Products, AAPS PharmScience, vol. 4, Issue 1, 2002, p. 1-5.
Mueller, Eugen Excerpt on biguanides, Methoden der Organisichen Chemie, 1952, p. 215-2019.
Bailey, fixed dose single table anti-diabetic combinations, Diabetes, Obesity and metabolism, vol. 11, 2009, p. 527-533.
Merck & Co, Januet Leaflet, 2008, Evidence of date of Disclosure, p. 1-24.
Supplementary Appendix of Gallwitz, Lancet, vol. 380, published online Jun. 28, 2012, p. 475-483.
Dedova, Alogorithims of Specialized Medical care for diabetes, 8th edition, Sugar Glabetes, vol. 1S, 2017, 31 pages.
"Betahistine diHCL CF 16 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG,P3_RVG1:H,EN,57626>.
"Betahistine diHCL CF 8 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG,P3_RVG1:H,EN,56227>.
"Sifrol 0,088 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70120>.
"Sifrol 0,18 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70121>.
"Sifrol 0,35 mg, tabletten," Dutch Medicines Evaluation Board, Dated Nov. 16, 1999, Retrieved online from: <http://db.cbg-meb.nl/ords/f?p=111:3:0:SEARCH:NO::P0_DOMAIN,P0_LANG,P3_RVG1:H,EN,70673>.
"Sifrol 0,70 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70122>.
"Sifrol 1,1 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70124>.
Abstract for AU 2003280680, Jun. 18, 2004.
Abstract for AU 2009224546, Sep. 17, 2009.
Abstract in English for DE10109021, 2002.
Abstract in English for DE19705233, Aug. 13, 1998.
Abstract in English for DE2205815, 1972.
Abstract in English for EP0023032, 1981.
Abstract in English for JP 2002/348279, Dec. 4, 2002.
Abstract in English for JP 2003/286287, Oct. 10, 2003.
Abstract in English for KR20070111099, Nov. 11, 2007.
ACTOS Prescribing Information, 1999, pp. 1-26.
Adams, Pub Pharmafile, 2011, Boehringer-lilly launch diabetes drug tradjenta in US.
Adebowale, K.O. et al., "Modification and properties of African yam bean (*Sphenostylis stenocarpa* Hochst. Ex A. Rich.) Harms starch I: Heat moisture treatments and annealing." Food Hydrocolloids, 2009, vol. 23, No. 7, pp. 1947-1957.
Ahmed, Materials Formulation of Low Dose Medicines, Americal Pharma review, vol. 3, 2000, 1 page.

(56) References Cited

OTHER PUBLICATIONS

Ahren, B. et al., "Twelve- and 52-Week Efficacy of the Dipeptidyl Peptidase IV Inhibitor LAF237 in Metformin-Treated Patients With Type 2 Diabetes." Diabetes Care, 2004, vol. 27, No. 12, pp. 2874-2880.

Ahren, Bo "Novel combination treatment of type 2 diabetes DPP-4 inhibition + metformin." Vascular Health and Risk Management, 2008, vol. 4, No. 2, pp. 383-394.

Ahren, Bo, et al.; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.

Ahren, Bo; "DPP-4 inhibitors", Best practice and research in clinical endocrinology and metabolism—New therapies for diabetes Dec. 2007 GB LNKD-DOI:10.1016/J. Beem.2007.07.005, vol. 21, No. 4, Dec. 2007, pp. 517-533.

Ahren, Vascular Health and Risk Management, Novel combination treatment of type 2 diabetes DPP-4 inhibition plus metformin, 2008, p. 383-394.

Al-Masri, I.M. et al., "Inhibition of dipeptidyl peptidase IV (DPP IV) is one of the mechanisms explaining the hypoglycemic effect of berberine." Journal of Enzyme Inhibition and Medicinal Chemistry, 2009, vol. 24, No. 5, pp. 1061-1066.

Alter, M. et al., "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.

American Association of Clinical Endocrinologists, "Medical Guidelines for Clinical Practice for the Management of Diabetes Mellitus." Endocrine Practice, 2007, col. 13, Suppl. 1, pp. 1-68.

American Diabetes Association, "Standards of Medical Care in Diabetes-2008." Diabetes Care, Jan. 2008, vol. 31, Supplement 1, pp. S12-S54.

Announcement of the approval of Novel oral Diabetes Drug JANUVIA, Press Release, 2006.

Anonymous, New England Journal of Medicine, The effect of intensive treatment of diabetes on the development and progession of long term complicationsin insulin dependent mellitus, vol. 329, 1993.

Anstee, Quentin M. et al. "Mouse models in non-alcholic fatty liver disease and steatohepatitis research" (2006) International Journal of Expermental Pathology, vol. 87, pp. 1-16.

Approval material for Tradjenta tablet, Trial 1218.2, Center for Drug Eval. and Research, 2011.

Aronow, Congestive Heart Failure, Treatment of Heart Failure in Older Persons with Coexisting Conditions, vol. 9, No. 3, 2003, p. 142-147.

Aschner, Emerging Treatments and Technologies, Effect of the Dipepttidyl Peptidase-4 Inhibitor Sitagliptin as Monotherapy on Glycemic Control in Patients with Type 2 Diabetes, vol. 29, 2006.

Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.

Augusti, D.V. et al., "Quantitative determination of the enantiomeric composition of thalidomide solutions by electrospray ionizatio tandem mass spectrometry". Chem Comm, 2002, p. 2242-2243.

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Aulinger, B.A. et al., "Ex-4 and the DPP-IV Inhibitor Vildagliptin have Additive Effects to Suppress Food Intake in Rodents". Abstract No. 1545-P, 2008.

Aulton, Michael E., Pharmaceutics: The Science of Dosage Form Design, Second Edition, 2002, pp. 441-448.

Baetta, R. et al., "Pharmacology of Dipeptidyl Peptidase-4 Inhibitors." Drugs, 2011, vol. 71, No. 11, pp. 1441-1467.

Balaban, Y.H. et al., "Dipeptidyl peptidase IV (DDP IV) in NASH patients" Annals of Hepatology, vol. 6, No. 4, Oct. 1, 2007, pp. 242-250, abstract.

Balbach, S. et al., "Pharmaceutical evaluation of early development candidates the 100 mg-approach." International Journal of Pharmaceutics, 2004, vol. 275, pp. 1-12.

Balkan, B. et al., "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.

Banker, Gilbert S., "Prodrugs." Modern Pharmaceutics Third Edition, Marcel Dekker, Inc., 1996, p. 596.

Barrara, Granulation, Handbook of Powder Technology, vol. 11, 2015, 2 pages.

Basi, Diabetes Care, vol. 31, 2008, 1 page.

Bastin, R.J. et al., "Salt Selection and Optimization Procedures for Pharmaceutical New Chemical Entities". Organic Process Research and Development, 2000, vol. 4, p. 427-435.

Beauglehole, Anthony R., "N3-Substituted Xanthines as Irreversible Adenosine Receptor Antagonists." Ph.D. Thesis, Deakin University, Australia, 2000, pp. 1-168.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Zander, M. et al., "Additive Glucose-Lowering Effects of Glucagon-Like Peptide-1 and Metformin in Type 2 Diabetes." Diabetes Care, 2001, vol. 24, No. 4, pp. 720-725.

Zeeuw, D. et al., "Albuminuria, a Therapeutic Target for Cardiovascular Protection in Type 2 Diabetic Patients With Nephropathy." Circulation, 2004, vol. 110, No. 8, pp. 921-927.

Zejc, Alfred, et al; "Badania Nad Piperazynowymi Pochodnymi Dwumetyloksantyn" Acta Polon Pharm, XXXV (1976) Nr. 4 pp. 417-421.

Zeng, "Efficacy and Safety of linagliptin added to metformin and sulphonylurea in Chinese patients with type 2 diabetes: a sub-analysis of data from a randomised clinical trial", Current Medical Research and Opinion, 2013, 8 pages.

Zerilli, T. et al., "Sitagliptin Phosphate: A DPP-4 Inhibitor for the Treatment of Type 2 Diabetes Mellitus." Clinical Therapeutics, 2007, vol. 29, No. 12, pp. 2614-2634.

Zhang, Classification and Treatment Prinicples of Diabetes, Beijing Medical Univ and China Union Medical Univ. Joint Publishing House. 1st ed., 1998, p. 939.

Zhimei, Xiao et al., "Study progression of oral drugs for treatment of type II diabetes." Drug Evaluation, 2004, vol. 1, No. 2, pp. 138-143.

Zhong, Qing et al; "Glucose-dependent insulinotropic peptide stimulates proliferation and TGF-? release from MG-63 cells," Peptides 24 (2003) 611-616.

Zhu, G. et al., "Stabilization of Proteins Encapsulated in Cylindrical Poly(lactide-co-glycolide) Implants: Mechanism of Stabilization by Basic Additives." Pharmaceutical Research, 2000, vol. 17, No. 3, pp. 351-357.

Zimdahl, H. et al., "Influence of TCF7L2 gene variants on the therapeutic response to the dipeptidylpeptidase-4 inhibitor linagliptin." Diabetologia, 2014, vol. 57, pp. 1869-1875.

Zimmer et al; Synthesis of 8-Substituted Xanthines and their Oxidative Skeleton Rearrangement to 1-Oxo-2,4,7,9-tetraazaspiro[4,5]dec-2-ene-6,8, 10-triones; Euripean Journal Organic Chemistry (1999) vol. 9 pp. 2419-2428.

The 4th Edition, Experimental Chem., Course 1, Society of Japan, 1990, p. 184-186.

Snyder, Use of Insulin and Oral hypoglycemic medication in patients with diabetes mellitus and advanced kidney disease, Diabetic Medication in Kidney Disease, Seminars in Dialysis, vol. 17, 2004, p. 365-370.

Xie, Hypoglycemic Drugs, New Practical Pharmacy, 2007, p. 832-934.

Akiyama, Sulphostin, a potent Inhibitor for dipeptiyl peptidase IV, The Journal of Antibiotics, vol. 54, No. 9, 2001, p. 744-746.

Artunc, Expert opinion relating to Euro patent Ep2640371, May 11, 2022, 5 pages.

(56) References Cited

OTHER PUBLICATIONS

Wong, Endothelial Dysfunction, J. Cardiovasc Pharmacol, vol. 55, 2010, 8 pages.
Groop, Linagliptin and its effects on hyperglycemia, Diabetes and obes Metab vol. 10, 2017, 10 pages.
Wang, A modest decease in endothelial NOS in mice, PNAS vol. 108, 2011, 7 pages.
Du, Hyperglycemia inhibits endothelial nitric oxide synthase oxide activity, JCI, vol. 108, 2001, 9 pages.
Craven, Impaired nitric oxide release by glomeruli from diabetic rats, Metabolism, vol. 44, 1995, 4 pages.
Excerpts of Diabetologie in Klinik and Praxis, 5th Edition, 2003, pp. 384 and 434.
Nippon Boehringer Ingelheim Co., Ltd., Press Release, Linagliptin Showing improvement in Albuminuria, Jun. 18, 2012.
Japanese Society of Nephrology, Clinical Practice Guidebook, 2012, 145 pages.
Lee, Radical Approach to Diabetic Neuropathy, Kidney International, vol. 72, 2007, p. 67-70.
Rungby, inhibition of dipeptidyl peptidase 4 by BI 1356, a new drug for the treatment of beta cell failure in type 2 diabetes, Expert Opin. Invest. Drugs, vol. 18, 2009, p. 835-838.
Hahr, Management of diabetes mellitus in patients with chronic kidney disease, Clinical Diabetes and Endocrinology, vol. 10, 2015, 9 pages.
Duong, Population pharmacokinetics of metformin in healthy subjects and patients with type 2 diabetes, Clinical Pharmacokinetics, vol. 52, 2013, p. 373.
Bell, Prescribing for older people with chronic renal impairment, Australian Family Physician, vol. 42, 2013, 5 pages.
Munar, Drug dosing adjustments in patients with chronic kidney disease, AFP, vol. 75, 2007, 10 pages.
Laasko, Hyperglycemia and Cardiovascular Disease in Type 2 Diabetes, Diabetes, vol. 48, 1999, 6 pages.
Haffner, Mortality from coronary heart disease in subjects with type 2 diabetes and in nondiabetic subjects with and without prior myocardial infarction, The N.E. J. of Medicine, vol. 339, 1996, 6 pages.
Calles, Type 2 diabetes, Coronary Artery Disease, vol. 10, 1999, 8 pages.
Marks, Cardiovascular Risk in Diabetes, Journal of Diabetes and the complications, vol. 14, 2000, 8 pages.
Fadini, DPP-4 inhibition has no cute affect on BNP and its N-terminal pro-hormone measured by commercial immune assays, Cardiovascualr Diabetology, vol. 16, 2017, 7 pages.
Mu, Impact of DPP-4 inhibitors on plasma levels of BNP and NT-pro-BNP in type 2 diabetes mellitus, Diabetology, vol. 14, 2022, 9 pages.
McGuire, Linagliptin effects on heart failure and related outcomes in individuals with type 2 diabetes mellitus, http://shjajournals.org on Mar. 18, 2023, 11 pages.
Clifton, Do dipeptidyl Peptidase IV inhibitors cause heart failure?, Clinical therapeutics, vol. 36, 2014, 8 pages.
Shiraki, The DPP4 inhibitor linagliptin exacerbated heart failure due to energy deficiency, Pharmcology and Pharmacotherapy, downloaded from http://academic.cup.com/eurheartj/article/43/supplement_2/ehcac544268/26746435 Mar. 18, 2023.
Mu, Impact of DPP-4 inhibitors on plasma levels of BNP and NT-pro-BNP in type 2 diabetes mellitus, Diabetology and Diabetes Mellitus, vol. 14, 2022, 9 pages.
Kroller-Schuhmacher, Comparison of direct and indirect antioxidant effects of linagliptin with other gliptins, Vascular Pharmacology, vol. 56, 2012, p. 352.
Schuff, Comparison of the Direct and indirect Antioxidant Effects of DPP-4 Inhibitors, retrieved from https://professional.diabetes.org/abstract/comparison-direct-and-indirect-antioxidant-effects-dpp-4-inhitors-anti-inflammatory 2011, 1 page.
Singh, Sepsis in diabetes, Diabetes and metabolic Syndrome, Clinical Research and Reviews, vol. 5, 2011, p. 222-227.
Fink, Animal models of sepsis and its complications, Kidney International, vol. 74, 2008, p. 991-993.
Galley, Oxidative stress and mitochondrial dysfunction in sepsis, British J. of Anaesthesia, vol. 107, 2011, p. 57-64.
Baudouin, Sepsis, Springer-Verlag, vol. 88, 2008, p. 1-4.
Freeman, Efficacy and Safety of Linagliptin in Adults with type 2 diabetes, vol. 36, 2011, p. 807-842.
UK Prospective Diabetes Study Group, Intensive blood glucose control with sulphonylureas or insulin compared withconventional treatment and risk of complications in patients with type 2 diabetes, The Lancet, vol. 352, 1998, p. 837-853.
Scherbaum, Sepsis, Psychyrembel Worterbach Diabetologie, 2003.
Schuermann, The Didpeptidyl Peptidase-4 inhibitor linagliptin attentuates inflammation and accelerates epitheliaixation in wounds of diabetic ob/ob mice, J. of pharmacology and experimental therapeutics, 2012, 8 pages.
Bell, Diabetes Care, The frequent, forgotten, and and often fatal complication of diabetes, vol. 26, 2003, 9 pages.
Berge, S. et al., "Pharmaceutical Salts." Journal of Pharmaceutical Sciences, 1977, vol. 66, No. 1, pp. 1-19.
Bergmann, Decrease of serum dipeptidylpeptidase activity in severs sepsis patients, Clinica Chimica Acta 2002., p. 123-126.
Bernstein, Joel "Polymorphism in Molecular Crystals." Oxford University Press, 2002, p. 9.
Blech, S. et al., "The Metabolism and Disposition of the Oral Dipeptidyl Peptidase-4 Inhibitor, Linagliptin, in Humans", Drug Metabolism and Disposition, 2010, vol. 38, No. 4, p. 667-678.
*Boehringer Ingelheim Pharmceuticals, Inc. v. HEC Pharm Co., Ltd., et al.,* No. 15-cv-5982, United States District Court for the District of New Jersey, Dec. 8, 2016.
Boehringer Ingelheim Press Release: Boehringer Ingelheim's diabetes Pipeline continues to advance as the company announces conclusion of robust Phase III pivotal trials programme for linalgiptin, Small Molecules, Published Sep. 28, 2009, 2 pages.
Bollag, R.J. et al.; "Osteoblast-Derived Cells Express Functional Glucose-Dependent Insulinotropic Peptide Receptors," Endocrinology, vol. 141, No. 3, 2000, pp. 1228-1235.
Borloo, M. et al. "Dipeptidyl Peptidase IV: Development, Design, Synthesis and Biological Evaluation of Inhibitors." 1994, Universitaire Instelling Antwerpen, vol. 56, pp. 57-88.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Brittain, H.G., "Methods for the Characterization of Polymorphs: X-Ray Powder Diffraction," Polymorphism in Pharmaceutical Solids, 1999, p. 235-238.
Brittain, Polymorphism on Pharmaceutical Solids, Chapter 5 Generation of Polymorphs, vol. 95, 1999, p. 183-226.
Brosius, Mouse Models of Diabetic Neuropathy, JASN, vol. 20, 2009, 5 pages.
Bundgaard, H. "Design of prodrugs: Bioreversible derivatives for various functional groups and chemical entities". Royal Danish School of Pharmacy, 1985, p. 1-92.
Busso et al., "Circulating CD26 is Negatively Associated with Inflammation in Human and Experimental Arthritis," Am. J. Path., vol. 166, No. 2, Feb. 2005, pp. 433-442.
Byrn, Stephen R. "Solid-State Chemistry of Drugs." Academic Press, 1982, pp. 1-27.
Caira, M.R., "Crystalline polymorphism of organic compounds" Topics in Current Chemistry, Springer, Berlin, vol. 198, 1998, p. 163-208.

(56) References Cited

OTHER PUBLICATIONS

Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.
Canadian Diabetes Association, "Pharmacologic Management of Type 2 Diabetes." Canadian Journal of Diabetes, 2003, vol. 27, Suppl. 2, pp. S37-S42.
Canadian Pharmacists Association, Compendium of Pharmaceuticals and Specialties, "Zestril" 2004, pp. 2289-2293.
Cao, C. et al., "The clinical application of linagliptin in Asians." Therapeutics and Clinical Risk Management, 2015, vol. 11, pp. 1409-1419.
Castello, R. et al., "Discoloration of Tablets Containing Amines and Lactose." Journal of Pharmaceutical Sciences, 1962, vol. 51, No. 2, pp. 106-108.
Cefalu, Animal Models of Type 2 Diabetes: Clinical Presentation and Pathophysiological Relevance to the Human Condition, ILAR Journal, vol. 47, No. 3, 2006.
Chan, J.C. et al., "Safety and efficacy of sitagliptin in patients with type 2 diabetes and chronic renal insufficiency." 2008, Diabetes, Obesity and Metabolism, vol. 10, pp. 545-555.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Chaykovska, L. et al., "Effects of DPP-4 Inhibitors on the Heart in a Rat Model of Uremic Cardiomyopathy." www.plosone.org, 2011, vol. 6, No. 11, p. e27861.
ChemGaroo, "Leaving Group." 1999, Retrieved online: http://www.chemgapedia.de/vsengine/vlu/vsc/en/ch/12/oc/vluorganik/substitution/sn_2/sn2.vlu/Page/vsc/en/ch/12/oc/substitution/sn_2/abgangsgrupen/abgangsgruppe.vscml.html.
Chemical Abstract. EP412358, 1991:185517, Findeisen.
Chemical Abstract: FR2707641, 1995:543545, Dodey.
Chemical Abstract: No. 211513-37-0—Dalcetrapib. "Propanethioic acid, 2-methyl-, S-(2-[[[1-(2-ethylbutyl)cyclohexyl}carbonyl}amino}pheyl}ester". Formula: C23 H35 N O2 S. American Chemical Society. Sep. 20, 1998.
Chemical Abstract: No. 875446-37-0—Anacetrapib. "2-Oxazolidinone, 5-[3,5-bis(trifluoromethyl)phenyl]-3[[4'fluoro-2'-methoxy-5'-(1-methylethyl)-4-(trifluoromethyl)[1,1'-biphenyl]-2-yl]methyl]-4-methyl-,(4S,5R)-" Formula: C30 H25 F10 N O3. American Chemical Society, Feb. 28, 2006.
Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).
Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.
Chemical Abstracts Service, Database Accession number No. RN 668270-12-01, 2004, "1H-Purine-2,6-dione, 8-[(3R)-3-amino-1-piperidinyl]-7-(2-butyn-1-yl)-3,7-dihydro-3-methyl-1-[(4-methyl-2-quinazolinyl)methyl]".
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.
Cheon, et al., Biochemical Pharmacology, "Inhibition of dipeptidyl IV by novel inhibitors with pyrazolidine scaffold", 2005, vol. 70, p. 22-29.
Chiasson, J.-L. et al., "The Synergistic Effect of Miglitol Plus Metformin Combination Therapy in the Treatment of Type 2 Diabetes." Diabetes Care, 2001, vol. 24, No. 6, pp. 989-994.

Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.
Chowhan, Z.T. et al., Drug-Excipient Interaction Resulting from Powder Mixing IV: Role of Lubricants and Their Effect on In Vitro Dissolution, Journal of Pharmaceutical Sciences, 1986, vol. 75, No. 6, pp. 542-545.
Clarivate Analytics on STN: Confirmation of the public accessibility of Schmeider before May 31, 2011.
Clinical Journal of Chinese Medicine, vol. 3, 2008, p. 360-364.
Clinical Trial NCT00622284 (published online at clinicaltrials.gov on Feb. 22, 2008).
Clinical Trial Protocol, "A Randomised, Double-blind, Placebo-controlled, Five Parallel Groups Study Investigating the Efficacy and Safety of BI 1356 BS." Boehringer Ingelheim Pharmaceuticals, last updated on Jun. 24, 2014.
Clinical Trial results of Tradjenta Tablet, Center for Drug Evaluation and Research, 2010.
Clinical Trial, NCT00622284, clinicaltrials.gov, updated Feb. 22, 2008.
Clinical Trials NCT00601250, clinicaltrials.gov, Jan. 25, 2008.
Clinical trials, A Randomized, Double Blind, Active Controlled parallel Group Efficacy and Safety Study of BI 1356 Compared to Glimepiride over 2 years in Type 2 Diabetic Patients with insufficient glycemic control despite metformin therapy, https://clinicaltrials.gov/archive/NCT00622284/20120606, 2008.
Drug Data Report, 1994, Source, Smith Kline Beechman, Treatments for Septic Shock, p. 459.
Dugi, K. et al., "Safety, tolerability, pharmacokinetics, and pharmacodynamics of BI 1356, a novel DPP-IV inhibitor with a wide therapeutic window." Diabetic Medicine, 2006, vol. 23, Suppl. 4, p. 300.
Dunitz, J. et al., "Disappearing Polymorphs." Acc. Chem. Res. 1995, vol. 28, No. 4, pp. 193-200.
Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.
Eckhardt, "-(3-(R)-Aminopiperidin-1-yl)7-but-2-ynyl-3-methyl-1-(4-methyl-quinazolin-2-ylmethyl-3,7-dihydropurine-2,6-dione (BI 1356), a highly potent, selective, long-acting, and orally bioavailable DPP-4 inhibitor for the treatment of type 2 diabetes", J. med. Chem, vol. 50, 2007.
Eckhardt, 8-(3-(R)-Aminopiperidin-1-yl)-7-but-2-ynyl--3-methyl-1-(4-methyl-quinazolin-2-ylmethyl)-3,7-dihydropurine-2,6-dione (BO1356), Journal of Medicinal Chem., vol. 50, 2007, p. 6450-5453.
Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.
Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.
Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.
EMEA Guidelines on Eucreas®, 2007, pp. 1-27.
EMEA Guidelines on Galvus®, 2007, pp. 1-34.
EMEA: European Medicines Agency, "Galvus (vildagliptin)" Retrieved online on Jan. 21, 2016.
EMEA: European Medicines Agency, ICH Topic E4, "Dose Response Information to Support Drug Registration." 1994, pp. 1-10.
Encyclopedia of Pharma Technology, Swarbrick, 3rd Ed., vol. 1, Absorption of Solid Surfaces, 2007.
Ennis, Handbook of Pharmaceutical Granulation Technology, Theory of Granulation, 2010.

(56) References Cited

OTHER PUBLICATIONS

EU Clinical Trial Register, "A multicenter, international, rendomized, parallel group, double-blind, placebo-controlled, cardiovascular safety and renal microvascular outcome study with linagliptin, 5 mg once daily in patients with type 2 diabetes mellitus at high vascular risk." Aug. 19, 2015.
Eucreas Scientific Discussion, 2007, p. 1-27, www.emea.europa.eu/humandocs/PD/Fs/EPAR/eucreas/H-807-en6.pdf, Anonymous.
European Search Report for EP 08 15 9141 mailed Apr. 6, 2009 (European counterpart of U.S. Appl. No. 12/143,128).
Excerpt from Orange Book of Product Tradjenta, Feb. 5, 2011.
Eyjolfsson, Reynir "Lisinopril-Lactose Incompatibility." Drug Development and Industrial Pharmacy, 1998, vol. 24, No. 8, pp. 797-798.
Fantus, George, "Metformin's contraindications: needed for now." Canadian Medical Association Journal, 2005, vol. 173, No. 5, pp. 505-507.
Federal register, Department of Health and Human Services, vol. 62, 1997, 4 pages.
Feng, J. et al., "Discovery of Alogliptin: A Potent, Selective, Bioavailable, and Efficacious Inhibitor of Dipeptidyl Peptidase IV." Journal of Medicinal Chemistry, 2007, vol. 50, No. 10, pp. 2297-2300.
Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.
Ferry, Robert Jr., "Diabetes Causes." eMedicine Health, MedicineNet.com, 2013, Retrieved from internet on Aug. 22, 2013, <http://www.onhealth.com/diabetes_health/page3.htm#diabetes_causes>.
Fiorucci, et al. Trends in Molecular Medicine, Targeting farnesoid X receptor for liver and metabolic disorders, 13(7), 2007, p. 298-309.
Flatt, P.R. et al., "Dipeptidyl peptidase IV (DPP IV) and related molecules in type 2 diabetes." Frontiers in Bioscience, 2008, vol. 13, pp. 3648-3660.
Florez, J. et al. "TCF7L2 Polymorphisms and Progression to Diabetes in the Diabetes Prevention Program." The New England Journal of Medicine, 2006, vol. 355, No. 3, pp. 241-250.
Forst, ADA, Novel, Potent, Selective, DPP-4 inhibitor BI 1356 Significantly lowers HbA1c after only 4 weeks of treatment, 2007.
Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.
Forst, T. et al., "The oral DPP-4 inhibitor linagliptin significantly lowers HbA1c after 4 weeks of treatment in patients with type 2 diabetes mellitus." Diabetes, Obesity and Metabolism, 2011, vol. 13, pp. 542-550.
Freeman, Initial Combination therapy for patients with type 2 diabetes mellitus, Drugs in Context, 2013, p. 212256., 6 pages.
Fuguchi, Therapeutic Effects and Adverse Reactions to Oral Hypoglycemic Agents, Journal of the Nippon Hospital Pharmacists Assoc, 1976, vol. 1, p. 226-229, abstract only.
Fukushima et al., Drug for Treating Type II Diabetes (6), "action-mechanism of DPP-IV inhibitor and the availability thereof" Mebio, 2009, vol. 26, No. 8, pp. 50-58.
Gall, "Prevalence of micro-and macroalbuminuria, arterial hypertension, retinopathy and large vessel disease in European type 2 (non-insulin dependent) diabetic patients", Diabetologia (1991) 655-661.
Gallwitz, B. "Sitagliptin with Metformin: Profile of a Combination for the Treatment of Type 2 Diabetes". Drugs of Today, Oct. 2007, 43(10), p. 681-689.
Gallwitz, B. et al., "2-year efficacy and safety of linagliptin compared with glimepiride in patients with type 2 diabetes inadequately controlled on metformin: a randomised, double-blind, non-inferiority trial." Lancet, 2012, vol. 380, pp. 475-483.
Gallwitz, B. et al., "Saxagliptin, a dipeptidyl peptidase IV inhibitor for the treatment of type 2 diabetes". IDRUGS, vol. 11, No. 12, Dec. 2008, p. 906-917.
Gallwitz, B. et al., DPP IV inhibitors for the Treatment of Type 2 Diabetes; Diabetes Frontier (2007) vol. 18, No. 6 pp. 636-642.
Gallwitz, B., "Safety and efficacy of linagliptin in type 2 diabetes patients with common renal and cardiovascular risk factors." Therapeutic Advances in Endocrinology and Metabolism, 2013, vol. 4, No. 3, pp. 95-105.
Gallwitz, linagliptin—A novel Dipeptidyl Peptidase Inhibitor for Type 2 Diabetes Therapy, Clinical Medicine Indights: Endocrinology and Diabetes, 2012, vol. 5, p. 1-11.
Galvus (Vildagliptin) Scientific Discussion, EMEA, 2007, pp. 1-34.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Garber, A.J. et al., "Simultaneous glyburide/metformin therapy is superior to component monotherapy as an initial pharmacological treatment for type 2 diabetes." Diabetes, Obesity and Metabolism, 2002, vol. 4, pp. 201-208.
Garber, A.J. et al., "Update: Vildaglitin for the treatment of Type 2 diabetes" Expert Opinion on Investigational Drugs, 200801GB, vol. 17, No. 1, Jan. 2008, p. 105-113.
Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.
Geka, 2001, vol. 67, No. 11, p. 1295-1299.
Gennaro, Alfonso R. Remington Farmacia, 2003, Spanish copy: p. 828, English copy: pp. 711-712, Preformulation, Chapter 38.
Gennaro, Alfonso R., Remington Farmacia, 19th Edition, Spanish copy, 1995, p. 2470.
Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.
Thomas, L., "Chronic treatment with the Dipeptidase-4 Inhibitor BI 1356[9R]-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.
Thomas, Leo et al: "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor . . . " Journal of Pharmacology and Experimental Therapeutics, 2008, vol. 325, No. 1, pp. 177.
Thornber, C.W., "Isosterism and Molecular Modification in Drug Design." Chemical Society Reviews, 1979, pp. 563-580.
Tiwari, Linagliptin, A dipeptyl peptidase-4 inhibitor for the treatment of type 2 diabetes, Current Opinion in Ivestigational Drugs, vol. 10, 2009, p. 1091-1104.
Tounyoubyou, "Symposium-19: Future Perspectives on Incretion Therapy in Diabetes." 2008, vol. 51, Suppl. 1, p. S-71, S19-2.
Tradjenta, Highlights of Prescribing Information (revised Sep. 2012).
Tribulova, N. et al. "Chronic Disturbances in NO Production Results in Histochemical and Subcellular Alterations of the Rat Heart." Physiol. Res., 2000, vol. 49, No. 1, pp. 77-88.
Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.
Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013.
Turner, R.C. et al., "Glycemic Control With Diet, Sulfonylurea, Metformin, or Insulin in Patients With Type 2 Diabetes Mellitus Progressive Requirement for Multiple Therapies (UKPDS 49)" The Journal of the American Medical Association, 1999, vol. 281, No. 21, pp. 2005-2012.
U.S. Appl. No. 15/235,575, filed Aug. 12, 2016, Inventor: Klaus Dugi.
Uhlig-Laske, B. et al., "Linagliptin, a Potent and Selective DPP-4 Inhibitior, is Safe and Efficacious in Patients with Inadequately

(56) References Cited

OTHER PUBLICATIONS

Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.
United Healthcare, "Diabetes." Retrieved from internet on Aug. 22, 2013, http://www.uhc.com/source4women/health_topics/diabetesirelatedinformation/d0f0417b073bf11OVgnVCM1000002f1Ob1Oa _. htm.
US Court of Appeals for the Federal Circuit, *Boehringer Ingelheim Pharmaceuticals, Inc.* v. *Mylan Pharmaceuticals, Inc.*, Decided Mar. 16, 2020, retrieved online http;///www.cafc.uscourts.gov/sites/default/files/opinions-orders/19-1172.Opinion.3-16-2020_1551193.pdf (last visited May 29, 2020).
Van Heek, M. et al., "Ezetimibe, a Potent Cholesterol Absorption Inhibitor, Normalizes Combined Dyslipidemia in Obese Hyperinsulinemic Hamsters." Diabetes, 2001, vol. 50, pp. 1330-1335.
Vichayanrat, A. et al., "Efficacy and safety of voglibose in comparison with acarbose in type 2 diabetic patients." Diabetes Research and Clinical Practice, 2002, vol. 55, pp. 99-103.
Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.
Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.
Vincent, S.H. et al., "Metabolism and Excretion of the Dipeptidyl Peptidase 4 Inhibitor [14C]Sitagliptin in Humans." Drug Metabolism and Disposition, 2007, vol. 35, No. 4, pp. 533-538.
Wade, Organic Chem, 6th Edition, 2006, p. 918, 943-956.
Wang, Y. et al., "BI-1356. Dipeptidyl-Peptidase IV Inhibitor, Antidiabetic Agent." Drugs of the Future, 2008, vol. 33, No. 6, pp. 473-477.
Waterman, Accelerating aging-Prediction of Chemical Stability of Pharmaceuticals, International Journal of Pharmaceutics, 2005, vol. 293, p. 101-125.
Weber, Ann E., "Dipeptidyl Peptidase IV Inhibitors for the Treatment of Diabetes." Journal of Medicinal Chemistry, 2004, vol. 47, pp. 4135-4141.
WebMD, Autoimmune Diseases: What Are They? Who Gets Them? "What Are Autoimmune Disorders?" 2015, pp. 1-3. Retrieved online Jul. 9, 2015. http://www.webmd.com/a-to-z-guides/autoimmune-diseases.
Westerhuis, Optimisation of the composition and production of mannitol cellulose tablets International Journal of Pharmaceutics, 1996, p. 143, 151-162.
White, Cardiovascular Events in patients receiving alogliptin, Diabetes Pro, 2010, vol. 59, p. 391.
White, John R. Jr., "Dipeptidyl Peptidase-IV Inhibitors: Phamacological Profile and Clinical Use". Clinical Diabetes, Apr. 2008, vol. 26, No. 2, pp. 53-57.
Who drug information, International nonproprietary Names for Pharmaceutical Substances, vol. 23, 2009, 1 page.
Wikipedia, "Linagliptin" Sep. 12, 2015. <https://en.wikipedia.org/w/index.php?title=Linagliptin&oldid=333469979>.
Wikipedia, Annulation. Jun. 23, 2008, http://en.wikipedia.org/wiki/Annelation.
Wikipedia, Polyvinylpyrrolidone, https:en.wikipedia.org/wiki/access date May 15, 2018.
Wikipedia, the free encyclopedia, The carbonyl group, 2017, 1 page.
Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.

Wirth, D. et al., "Maillard Reaction of Lactose and Fluoxetine Hydrochloride, a Secondary Amine." Journal of Pharmaceutical Sciences, 1998, vol. 87, No. 1, pp. 31-39.
Witteles, R. M. et al., "Dipeptidyl Peptidase 4 Inhibition Increases Myocardial Glucose Uptake in Nonischemic Cardiomyopathy." Journal of Cardiac Failure, 2012, vol. 18, No. 10, pp. 804-809.
Wolff, M.E.: "Burger's Medicinal Chemistry and Drug Discovery" Fifth Edition, vol. 1: Principles and Practice, pp. 975-977, 1994, John Wiley & Sons, Inc.
World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.
Wu, Reactive Impurities in Excipients-Profiling, American Association of Pharmaceutical Scientists, 2011, vol. 12, No. 4, p. 1248-1263.
X-Ray Diffraction. The United States Pharmacopeia, 2002, USP 25 NF20, p. 2088-2089.
Yale, Jean-Francois, "Oral Antihyperglycemic Agents and Renal Disease: New Agents, New Concepts." Journal of the American Society of Nephrology, 2005, vol. 16, Suppl. 1, pp. S7-S10.
Yamagishi, S. et al., "Pleiotropic Effects of Glucagon-like Peptide-1 (GLP-1)-Based Therapies on Vascular Complications in Diabetes." Current Pharmaceutical Design, 2012, vol. 17, pp. 4379-4385.
Yamazaki, Comparison of Efficacies of a Dipeptidyl Peptidase IV Inhibitor and a-Glucosodase Inhibitors in Oral Carbohydrate and Meal Tolerance Tests and their Effects of their tolerance in mice, J. Pharmacol Science, 2007, p. 29-38.
Yap, W.S. et al., "Review of management of type 2 diabetes mellitus." Journal of Clinical Pharmacy and Therapeutics, 1998, vol. 23, pp. 457-465.
Yasuda, et al. "E3024 3-but-2-ynyl-5-methyl-2-piperazin-1-y1-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Yasuda, N. et al., "Metformin Causes Reduction of Food Intake and Body Weight Gain and Improvement of Glucose Intolerance in Combination with Dipeptidyl Peptidase IV Inhibitor in Zucker fa/fa Rats." The Journal of Pharmacology and Experimental Therapeutics, 2004, vol. 310, No. 2, pp. 614-619.
Yokoyama< "Prevalence of albumineria and renal insufficiency and associated clinical factors in type 2 diabetes: the Japan Diabetes clinical data Management study(JDDM15)" Nephrol Dial Transplant (2009) 24: 1212-1219 Advance Access Pub 2008.
Yoshikawa, Seiji et al.: Chemical Abstract of Japanese Patent No. WO 2003/104229 Preparation of purinone derivatives as dipeptidylpeptidase IV (DPP-IV) inhibitors, 2003.
Yoshioka, S. et al., "Stability of Drugs and Dosage Forms." Kluwer Academic Publishers, 2002, pp. 30-33.
Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.
Zaman, Comparison Between Effect of Vildagliptin and Linagliptin on Glycaemic control, renal function, liver funstion and lipid profile in patients of T2DM Inadequately controlled with combo of Metformin and Glimepiride, Journal of Dental and Medical Sciences, vol. 16, Issue 9, 2017. p. 27-31.
Groop, linagliptin lowers albuminaria on top of recommended standard treatment for diabetic nephropathy, Annual meeting Science Session American Diabetes Assoc., Jun. 6, 2012, Abstract, 1 page.
Wingard, Heart Disease and Diabetes, Diabetes in America, Chapter 19, 1995, p. 429-448.
Greer, Myocardial infarction and heart failure in the db/db diabetic mouse, Amer. J. Physio. Heart Circ. Physiol., vol. 290, 2006, p. H146-H153.
King, Microvascular and Macrovascular Complications of Diabetes, Amer. J. of Diabetes Complications, vol. 69, 2005, Article 87.
Japan Council for Quality Health Care, Guidlines for Treatment Chronic Heart Failure, https://minds.jcqhc.or.jp/n/med//4/me00/49/G0000132/0003 edited 2005.

(56) References Cited

OTHER PUBLICATIONS

Gennaro, Alfonso; Remington: The Science and Practice of Pharmacy, Twentieth Edition, 2000, Chapter 45, pp. 860-869.
Giron, D.; Thermal Analysis and Calorimetric Methods in the Characterisation of Polymorphs and Solvates; Thermochimica Acta (1995) vol. 248 pp. 1-59.
GLUCOPHAGE® Prescribing Information, 2001.
Glucotrol XL (glipizide), package insert, Pfizer, Apr. 1, 2002.
Goldstein, L.A., et al., "Molecular cloning of seprase: a serine integral membrane protease from human melanoma." Biochimica et Biophysica Acta, vol. 1361, 1997, No. 1, pp. 11-19.
Gomez-Perez, et al., "Insulin Therapy:current alternatives", Arch. Med.Res. 36: p. 258-272 (2005).
Goodarzi, M.O. et al., "Metformin revisited: re-evaluation of its properties and role in the pharmacopoeia of modern antidiabetic agents." Diabetes, Obesity and Metabolism, 2005, vol. 7, pp. 654-665.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Graefe-Mody, U. et al., "Effect of Renal Impairment on the Pharmacokinetics of the Dipeptidyl Peptidase-4 Inhibitor Linagliptin." Diabetes, Obseity and Metabolism, 2011, pp. 939-946.
Greene, T.W, et al., "Protection for the Amino Group". Protective Groups in Organic Synthesis, 3rd edition, 1999, p. 494-653.
Greischel, et al., Drug Metabolism and Deposition, "The Dipeptidyl Peptidase-4 Inhibitor Linagliptin Exhibits Time- and Dpse-Dependent Localization in Kidney, Liver, and Intestine after Intravenous Dosing: Results from High Resolution Autoradiography in Rats", 2010, vol. 38, No. 9, p. 1443-1448.
Groop, Effects of The DPP-4inhibitor linagliptin on albuminuria in patients with type 2 diabetes, www.abstractsonline.com, 2013, 1 page.
Guglielmi, C. et al., "Latent autoimmune diabetes in the adults (LADA) in Asia: from pathogenesis and epidemiology to therapy." Diabetes/Metabolism Research and Reviews, 2012, vol. 28, Supplement 2, pp. 40-46.
Gupta, V. et al., "Choosing a Gliptin." Indian Journal of Endocrinology and Metabolism, 2011, vol. 15, No. 4, pp. 298-308.
Gwaltney, S. "Medicinal Chemistry Approaches to the Inhibition of Dipeptidyl Peptidase IV", Current Topics in Medicinal Chemistry, 2008, 8, p. 1545-1552.
Gwaltney, S.L. II et al., "Inhibitors of Dipeptidyl Peptidase 4." Annual Reports in Medicinal Chemistry, 2005, vol. 40, pp. 149-165.
Haak, Initial Combination of linagliptin and metformin improves glycemic control in type 2 diabetes, Diabetes, Obesity and Metabolism, vol. 14, 2012, p. 565-574.
Hainer, Vojtech MD, PHD "Comparative Efficiency and Safety of Pharmacological Approaches to the Management of Obesity." Diabetes Care, 2011, vol. 34, Suppl. 2, pp. S349-S354.
Halimi, "Combination treatment in the management of type 2 diabetes: focus on vildagliptin and metformin as a single tablet", Vascular Health and Risk Management, 2008 481-92.
Halimi, S. et al., "Combination treatment in the management of type 2 diabetes: focus on vildagliptin and metformin as a single tablet." Vascular Health and Risk Management, 2008, vol. 4, No. 3, pp. 481-492.
Haluzik, M. et al., "Renal Effects of DPP-4 Inhibitors: A Focus on Microalbuminuria." International Journal of Endocrinology, 2013, vol. 35, No. 6, pp. 1-7.
Hammouda, Y. et al., "Lactose-induced Discoloration of Amino Drugs in Solid Dosage Form." Die Pharmazie, 1971, vol. 26, p. 181.
Han, Basic and Clinical Coronary Heart Disease, Jilin Univ. Press, 2012, p. 114-118.
Hanrimwon, Pharmaceutics Subcommitee, 2000, p. 321-322.
Hanrinwon, Pharmaceutical Subcommittee, Pharmaceutics, p. 284-288, 1995.
Hansen, European Journal of Pharmacology, "The DPP-IV inhibitor linagliptin and GLP-1 induce synergistic effects on body weight loss and appetite suppression in the diet-induced obese rat", 2014, p. 254-263.
Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.
Hashida, Mitsuru, "Strategies for designing and developing oral administration formulations." Yakuji-Jiho, Inc., 1995, pp. 50-51 and 89.
Hayashi, Michio., "Recipe for Oral Hypoglycemic Agents to Pathological Condition" Pharmacy (2006) vol. 57, No. 9 pp. 2735-2739.
He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.
He, Y.L. et al., "The influence of hepatic impariment on the pharmacokinetics f the dipeptidyl peptidase IV (DPP-4) inhibitor vildagliptin" European Journal of Clinical Pharmacology, vol. 63, No. 7, May 8, 2007, p. 677-686.
He, Y.L. et al., "The Influence of Renal Impairment on the Pharmacokinetics of Vildagliptin." Clinical Pharmacology & Therapeutics, 2007, vol. 81, Suppl. 1, Abstract No. PIII-86.
Headland, K. et al., "The Effect of Combination Linagliptin and Voglibose on Glucose Control and Body Weight." 73rd Annual Meeting Science Session, ADA, Chicago, Jun. 21, 2013.
Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.
Heise, et al., Diabetes, Obesity and Metabolism, "Pharmacokinetics, pharmacokinetics and tolerability of mutilple oral doses of linagliptin, a dipeptidyl peptidase-4 inhibitor in male type 2 diabetes patients", 2009, vol. 11, No. 8, p. 786-794.
Heise, T. et al., "Treatment with BI 1356, a Novel and Potent DPP-IV Inhibitor, Significantly Reduces Glucose Excursions after an oGTT in Patients with Type 2 Diabetes." A Journal of the American Diabetes Association, Jun. 2007, vol. 56, Supplement 1, Poster No. 0588P.
Heizmann, Xanthines as scaffold for molecular diversity, Molecular diversity, vol. 2, 1996, p. 171-174.
Herman, G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.
Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Hermann, Robert, et al; Lack of Association of PAX4 Gene with Type 1 Diabetes in the Hungarian Populations; Diabetes (2005) vol. 54 pp. 2816-2819.
Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.
Hilfiker, R. et al., "Relevance of Solid-state Properties for Pharmaceutical Products." Polymorphism in the Pharmaceutical Industry, 2006, Chapter 1, pp. 1-19.
Hinke, S.A. et al., "Metformin Effects on Dipeptidylpeptidase IV Degradation of Glucagon-like Peptide-1." Biochemical and Biophysical Research Communications, 2002, vol. 291, No. 5, pp. 1302-1308.
Hinke, S.A. et al., "On Combination Therapy of Diabetes With Metformin and Dipeptidyl Peptidase IV Inhibitors." Diabetes Care, 2002, vol. 25, No. 8, pp. 1490-1492.
Hinnen, D. et al., "Incretin Mimetics and DPP-IV Inhibitors: New Paradigms for the Treatment of Type 2 Diabetes." Journal Of The American Board of Family Medicine, 2006, vol. 19, No. 6, pp. 612-620.

(56) References Cited

OTHER PUBLICATIONS

Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.
Hocher, B. et al., "The novel DPP-4 inhibitors linagliptin and BI 14361 reduce infarct size after myocardial ischemia/ reperfusion in rats." International Journal of Cardiology, 2013, vol. 167, pp. 87-93.
Holman, et al., "Addition of biphasic, prandial, or basal insulin to oral therapy in type 2 diabetes", N. England Journal Medicine, p. 1716-1730, 2007.
Holst, Role on incretin hormones in the regulation of insulin, Am j. Physiol Endocrinol Metab., 2004.
Horie, Biomedcentral, Design, statistical analysis and sample size calculation of a phase IIb/III study of linagliptin vs. voglibose and placebo, 2009.
The Japan Diabetes Study, Practice Guidelines of Diabetes based on Scientific basis, Nankodo Co., 2004, p. 5-19, 37-56, 67-80, 93-121, 131-153.
Hanafusa, ABC18 for new diagnostics and treatments, The Medical Frontline, 2004, p. 79-86, 106-113.
Sakura, Trends in development in oral diabetic agents and new developments of treatment, foundations and clinics of biguanide, therapeutic positioning of a-glucosidase inhibitors, current state of development on new forms of therapeutic agents such as GIP, GIP-1 and th elike, Clinical Endocrinology, 2005, vol. 53, p. 9-15, 35-39, 51-59, 115-119.
Yoshimoto, Structure of DPP-4 and antidiabetic therapeutic agents, Current diabetology, vol. 3, 2001 p. 51-55.
Ministry of Health, Clinical Pharmacokinetics exam for Drugs, Pharma Affairs Bureau, 2001.
Bi Japan, Interview form for Trazenta Tabs 5mg, 18 ed., 2022.
Hayashi, Biguanides, Pharmacy, vol. 57, 2006, p. 9-13.
Matsumiya, Therapeutic agent for clinician, Diagnostics and Treatments, vol. 96, 2008, p. 389-390.
Takada, Admin of cardio drugs during renal function, Med and Drug Journal, 2003, p. 13-21.
Greenblatt, Pharmacokinetics in clinical practice, Shinko, 1989, p. 39-53.
Murata, Integrated essentials, Nankodo, 1984, p. 310-316.
Hirata, Kidney failure and medication, Jiho, 2005, p. 55-78.
Sasaki, If there is evden the slightest suspicion of renal dysfunction, renally excretory drugs should not be administered in regualr doses, Therapeutics, vol. 85, 2003, p. 541-543.
Yasuhara, Pharmacodynamics excretion, Clin. Pharmacology, vol. 30, 1999, p. 625-628.
The Japan diabetes Society, Guidelines for treatment of Diabetes 2006, p. 12.
Wingard, Heart Disease and Diabetes, Chapter 19, 2020, 20 pages.
Yoshimoto, DPP-4 structure, Latest Diabetes Treatments, vol. 4 pages.
Takada, Kidney Function and Drug Elimination, How to give a Cardiovascular Drug in Renal Function, vol. 3, 2003, 7 pages.

* cited by examiner

USES OF DPP IV INHIBITORS

This application claims priority of EP 06 009 203, which is hereby incorporated by reference in its entirety.

BACKGROUND OF THE INVENTION

1. Field of the Invention

The specification describes the use of selected DPP IV inhibitors for the treatment of physiological functional disorders and for reducing the risk of the occurrence of such functional disorders in at-risk patient groups. In addition, the use of the above-mentioned DPP IV inhibitors in conjunction with other active substances is described, by means of which improved treatment outcomes can be achieved. These applications may be used to prepare corresponding medicaments.

2. Description of the Prior Art

The enzyme DPP-IV, also known by the name CD26, is a serine protease which promotes the cleaving of dipeptides in proteins with a proline or alanine group at the N-terminal end. DPP-IV inhibitors thereby influence the plasma level of bioactive peptides including the peptide GLP-1 and are highly promising molecules for the treatment of diabetes mellitus.

Type 1 diabetes mellitus, which occurs mainly in juveniles under 30 years of age, is categorised as an autoimmune disease. With a corresponding genetic disposition and under the influence of various factors, insulitis occurs, followed by destruction of the B-cells, so that the pancreas is no longer able to produce much, if any, insulin.

Type 2 diabetes mellitus is not categorised as an autoimmune disease and manifests itself in a fasting blood sugar level exceeding 125 mg of glucose per dl of plasma; the measurement of blood glucose values is a standard procedure in routine medical analysis. Prediabetes is suspected if the fasting blood sugar level exceeds the maximum normal level of 99 mg of glucose per dl of plasma but does not exceed the threshold of 125 mg of glucose per dl of plasma, which is relevant for diabetes. This is also referred to as pathological fasting glucose (impaired fasting glucose). Another indication of prediabetes is a disrupted glucose tolerance, i.e. a blood sugar level of 140-199 mg of glucose per dl of plasma 2 hours after taking 75 mg of glucose on an empty stomach within the scope of an oral glucose tolerance test.

If a glucose tolerance test is carried out, the blood sugar level of a diabetic will be in excess of 199 mg of glucose per dl of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject the blood sugar level will be between 60 and 99 mg per dl of plasma before taking the glucose, less than 200 mg per dl 1 hour after taking it and less than 140 mg per dl after 2 hours. If after 2 hours the value is between 140 and 199 mg this is regarded as abnormal glucose tolerance or in some cases glucose intolerance.

In the monitoring of the treatment of diabetes mellitus the HbA1c value, the product of a non-enzymatic glycation of the haemoglobin B chain, is of exceptional importance. As its formation depends essentially on the blood sugar level and the life time of the erythrocytes the HbA1c in the sense of a "blood sugar memory" reflects the average blood sugar level of the preceding 4-12 weeks. Diabetic patients whose HbA1c level has been well controlled over a long time by more intensive diabetes treatment (i.e. <6.5% of the total haemoglobin in the sample) are significantly better protected from diabetic microangiopathy. The available treatments for diabetes can give the diabetic an average improvement in their HbA1c level of the order of 1.0-1.5%. This reduction in the HbA1C level is not sufficient in all diabetics to bring them into the desired target range of <6.5% and preferably <6% HbA1c.

If insulin resistance can be detected this is a particularly strong indication of the presence of the complex metabolic disorder of prediabetes. Thus, it may be that in order to maintain glucose homoeostasis a person needs 2-3 times as much insulin as another person. The most certain method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. Another method of measurement is the mathematical HOMA model. The insulin resistance is calculated by means of the fasting plasma glucose and the fasting insulin concentration. In this method it is not possible to distinguish between hepatic and peripheral insulin resistance. These processes are not really suitable for evaluating insulin resistance in daily practice. As a rule, other parameters are used in everyday clinical practice to assess insulin resistance. Preferably, the patient's triglyceride concentration is used, for example, as increased triglyceride levels correlate significantly with the presence of insulin resistance.

To simply somewhat, in practice it is assumed that people are insulin-resistant if they have at least 2 of the following characteristics:
1) overweight or obesity
2) high blood pressure
3) dyslipidaemia (an altered content of total lipids in the blood)
4) at least one close relative in whom abnormal glucose tolerance or type 2 diabetes has been diagnosed.

Overweight means in this instance that the Body Mass Index (BMI) is between 25 and 30 kg/m$^2$, the BMI being the quotient of the body weight in kg and the square of the height in metres. In manifest obesity the BMI is 30 kg/m$^2$ or more.

It is immediately apparent, from the above definition of insulin resistance, that hypotensive agents are suitable and indicated for treating it if, among other things, high blood pressure is found in the patient.

A similar indication of prediabetes is if the conditions for metabolic syndrome are met, the main feature of which is insulin resistance. According to the ATP IHINCEP Guidelines (Executive Summary of the Third Report of the National Cholesterol Education Program (NCEP) in the Journal of the American Medical Association 285:2486-2497, 2001) metabolic syndrome is present if a patient has at least 3 of the following characteristics:

1) Abdominal obesity, defined as a waist measurement of >40 inches or 102 cm in men and >35 inches or 94 cm in women 2) Triglyceride levels >150 mg/dl 3) HDL-cholesterol levels <40 mg/dl in men 4) High blood pressure >130/>85 mm Hg 5) Fasting blood sugar of >110 mg/dl This definition of metabolic syndrome immediately shows that hypotensives are suitable for treating it if the patient is found to have high blood pressure, among other things.

A triglyceride blood level of more than 150 mg/dl also indicates the presence of pre-diabetes. This suspicion is confirmed by a low blood level for HDL cholesterol. In women, levels below 55 mg per dl of plasma are regarded as too low while in men levels below 45 mg per dl of plasma are regarded as too low. Triglycerides and HDL cholesterol in the blood can also be determined by standard methods in medical analysis and are described for example in Thomas L (Editor): "Labor und Diagnose", TH-Books Verlagsgesellschaft mbH, Frankfurt/Main, 2000. A suspicion of prediabetes is further confirmed if the fasting blood sugar levels also exceed 99 mg of glucose per dl of plasma.

The term gestational diabetes (diabetes of pregnancy) denotes a form of the sugar disease which develops during pregnancy and usually ceases again immediately after the birth. Gestational diabetes is diagnosed by a screening test which is carried out between the 24th and 28th weeks of pregnancy. It is usually a simple test in which the blood sugar level is measured one hour after the administration of 50 g of glucose solution. If this 1 h level is above 140 mg/dl, gestational diabetes is suspected. Final confirmation may be obtained by a standard glucose tolerance test with 75 g of glucose.

Hyperglycaemia describes a functional disorder in which an excessively high glucose level is measured in the blood, either in the fasting state (increased glucose level of 100-125 mg/dl or diabetic-hyperglycaemic level of >125 mg/dl compared with the normal level of <100 mg/dl) or in non-fasting state (elevated glucose level of >180 mg/dl).

By adrenergic postprandial syndrome (reactive hypoglycaemia) the clinician means a functional disorder in which a disproportionately high insulin level leads to a drop in the blood sugar level (hypoglycaemia) caused by an imbalance between rapidly digested carbohydrates and a high insulin level persisting after a meal.

The term diabetic foot refers to lesions on the foot caused by diabetes mellitus, the primary cause of which is a polyneuropathy that can be put down to inadequate metabolic control. A diabetic foot is diagnosed by the occurrence of typical lesions (e.g. ulcers) in an existing case of diabetes mellitus.

The term diabetes-associated ulcer refers to an ulcerous inflammatory skin defect in a patient with diabetes mellitus. A diabetes-associated ulcer is diagnosed by typical anamnesis and physical examination (e.g. inspection of the foot).

The term diabetic hyperlipidaemia is used if a patient with diabetes mellitus suffers an increase in total cholesterol or, more typically in diabetic hyperlipidaemia, an increase in the plasma triglycerides, with or without a reduction in HDL cholesterol.

The term diabetic dyslipidaemia is used if the total cholesterol is not raised but the distribution of HDL- and LDL-cholesterol is altered, i.e. the patient's HDL cholesterol level is too low (e.g. <55 mg/dl for women and <45 mg/dl for men).

The term heart failure is used if either subjective symptoms or objective findings indicate an inability of the heart to achieve the necessary ejection output. Subjective symptoms may be e.g. difficulty breathing under stress or at rest. Objective findings include a reduced ejection output of the heart according to ultrasound (reduced ejection volume), congestion of the lungs according to X-ray, and/or reduced walking distances.

DETAILED DESCRIPTION OF THE INVENTION

Some selected DPP IV inhibitors are particularly suitable for the preparation of a medicament for the therapeutic treatment of patients who have been diagnosed with a medical or physiological functional disorder selected from among pre-diabetes, glucose intolerance (impaired glucose tolerance), pathological fasting glucose (impaired fasting glucose), diabetic foot, diabetes-associated ulcer, diabetic hyperlipidaemia, diabetic dyslipidaemia, newly diagnosed type 1 diabetes (to maintain a residual secretion of insulin from the pancreas), gestational diabetes (diabetes of pregnancy), hyperglycaemia, adrenergic postprandial syndrome (reactive hypoglycaemia) or heart failure.

These medicaments may also be used to reduce the risk that in spite of treatment the patient will suffer an impaired glucose metabolism, an elevated HbA1c value, an impaired fasting glucose value, manifest type 2 diabetes, a diabetic foot, a diabetes-associated ulcer, diabetic hyperlipidaemia or diabetic dyslipidaemia, and that in spite of the therapy insulin treatment will become necessary or macrovascular complications will occur.

Examples of macrovascular complications of this kind are myocardial infarct, acute coronary syndrome, unstable angina pectoris, stable angina pectoris, haemorrhagic or ischaemic stroke, peripheral arterial occlusive disease, cardiomyopathy, left heart insufficiency, right heart insufficiency, global heart insufficiency, heart rhythm disorders and vascular restenosis. These macrovascular complications are known to the skilled man and described in detail in the standard textbooks.

In addition the substances are suitable for enhancing the vitality and secretion capacity of cells after the transplanting of islets of Langerhans or beta cells, and thereby ensuring a favourable outcome after transplantation. The substances may also be used during the isolation and transplantation phase of islets of Langerhans or beta cells, by adding the specified substances to the conventional isolation or storage medium in a suitable concentration of 1 nmol/l to 1 µmol/l, preferably in a concentration of 1 nmol/l to 100 nmol/l. This results in an improvement in the quality of the material to be transplanted. An improvement in quality is obtained particularly in combination with added amounts of GLP-1 (glucagon like peptide 1), preferably in a concentration of 1-100 nmol/l. Corresponding isolation or storage media and corresponding methods of enhancing the vitality and secretion capacity of islets of Langerhans or beta cells by the addition of DPP IV inhibitors to the media used are a further object of the invention.

Finally, the above-mentioned inhibitors are suitable for the treatment of various forms of arthritis, but particularly rheumatoid arthritis.

DPP IV inhibitors selected according to the present invention can be described by formula (I)

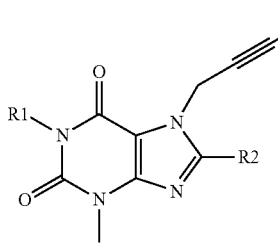

or formula (II)

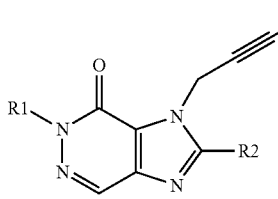

wherein R1 denotes ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl and R2 denotes 3-(R)-amino-piperidin-1-yl, (2-amino-2-methyl-propyl)-methylamino or (2-(S)-amino-propyl)-methylamino.

Particularly preferred DPP IV inhibitors are the following compounds and the therapeutically active salts thereof:

1-[(4-methyl-quinazolin-2-yl)methyl]-3-methyl-7-(2-butyn-1-yl)-8-(3-(R)-amino-piperidin-1-yl)-xanthine (cf. WO 2004/018468, Example 2(142)):

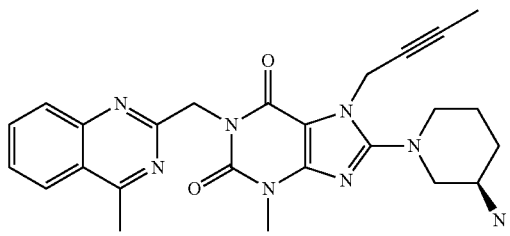 [SMILES: CC#CCn1c(N2CCC[C@@H](N)C2)nc2c1c(=O)n(Cc1nc(C)c3ccccc3n1)c(=O)n2C]

1-[([1,5]naphthyridin-2-yl)methyl]-3-methyl-7-(2-butyn-1-yl)-8-((R)-3-amino-piperidin-1-yl)-xanthine (cf. WO 2004/018468, Example 2(252)):

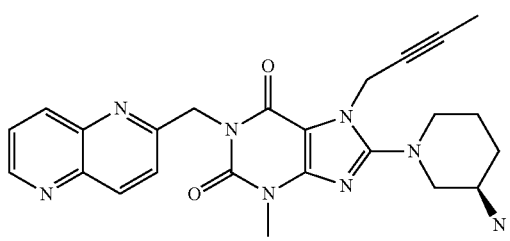 [SMILES: CC#CCn1c(N2CCC[C@@H](N)C2)nc2c1c(=O)n(Cc1ccc3ncccc3n1)c(=O)n2C]

1-[(quinazolin-2-yl)methyl]-3-methyl-7-(2-butyn-1-yl)-8-((R)-3-amino-piperidin-1-yl)-xanthine (cf. WO 2004/018468, Example 2(80)):

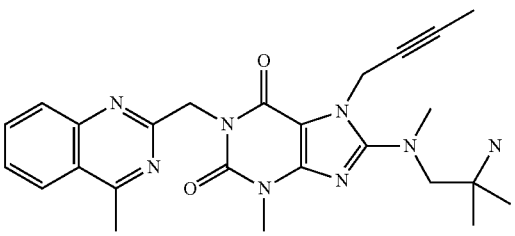 [SMILES: CC#CCn1c(N(C)CC(C)(C)N)nc2c1c(=O)n(Cc1nc(C)c3ccccc3n1)c(=O)n2C]

2-((R)-3-amino-piperidin-1-yl)-3-(but-2-ynyl)-5-(4-methyl-quinazolin-2-ylmethyl)-3,5-dihydro-imidazo[4,5-d]pyridazin-4-on (cf. WO 2004/050658, Example 136):

1-[(4-methyl-quinazolin-2-yl)methyl]-3-methyl-7-(2-butyn-1-yl)-8-[(2-amino-2-methyl-propyl)-methyl-amino]-xanthine (cf. WO 2006/029769, Example 2(1)):

1-[(3-cyano-quinolin-2-yl)methyl]-3-methyl-7-(2-butyn-1-yl)-8-((R)-3-amino-piperidin-1-yl)-xanthine (cf. WO 2005/085246, Example 1(30)):

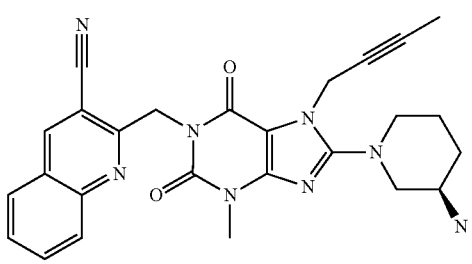 [SMILES: CC#CCn1c(N2CCC[C@@H](N)C2)nc2c1c(=O)n(Cc1nc3ccccc3cc1C#N)c(=O)n2C]

1-(2-cyano-benzyl)-3-methyl-7-(2-butyn-1-yl)-8-((R)-3-amino-piperidin-1-yl)-xanthine (cf. WO 2005/085246, Example 1(39)):

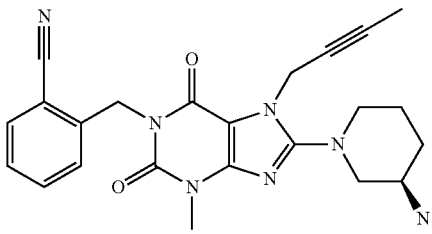 [SMILES: CC#CCn1c(N2CCC[C@@H](N)C2)nc2c1c(=O)n(Cc1ccccc1C#N)c(=O)n2C]

1-[(4-methyl-quinazolin-2-yl)methyl]-3-methyl-7-(2-butyn-1-yl)-8-[(S)-(2-amino-propyl)-methylamino]-xanthine (cf. WO 2006/029769, Example 2(4)):

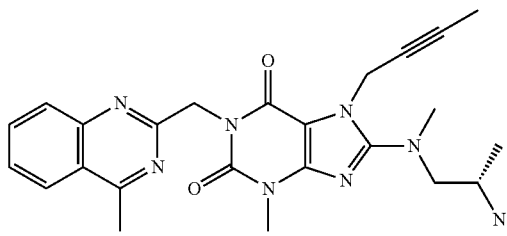 [SMILES: CC#CCn1c(N(C)C[C@H](C)N)nc2c1c(=O)n(Cc1nc(C)c3ccccc3n1)c(=O)n2C]

1-[(3-cyano-pyridin-2-yl)methyl]-3-methyl-7-(2-butyn-1-yl)-8-((R)-3-amino-piperidin-1-yl)-xanthine (cf. WO 2005/085246, Example 1(52)):

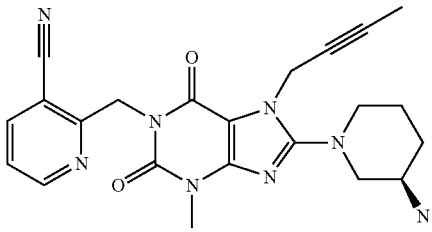

1-[(4-methyl-pyrimidin-2-yl)methyl]-3-methyl-7-(2-butyn-1-yl)-8-((R)-3-amino-piperidin-1-yl)-xanthine (cf. WO 2005/085246, Example 1(81)):

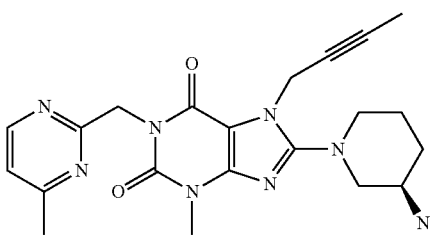 [SMILES: CC#CCn1c(N2CCC[C@@H](N)C2)nc2c1c(=O)n(Cc1nccc(C)n1)c(=O)n2C]

1-[(4,6-dimethyl-pyrimidin-2-yl)methyl]-3-methyl-7-(2-butyn-1-yl)-8-((R)-3-amino-piperidin-1-yl)-xanthine (cf. WO 2005/085246, Example 1(82)):

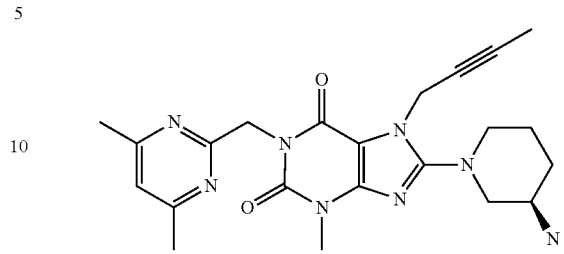

1-[(quinoxalin-6-yl)methyl]-3-methyl-7-(2-butyn-1-yl)-8-((R)-3-amino-piperidin-1-yl)-xanthine (cf. WO 2005/085246, Example 1(83)):

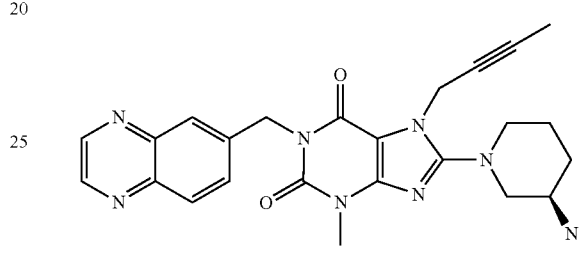

These DPP IV inhibitors are distinguished from structurally comparable DPP IV inhibitors, as they combine exceptional potency and a long-lasting effect with favourable pharmacological properties, receptor selectivity and a favourable side-effect profile or bring about unexpected therapeutic advantages or improvements when combined with other pharmaceutical active substances. Their preparation is disclosed in the publications mentioned.

As different metabolic functional disorders often occur simultaneously, it is quite often indicated to combine a number of different active principles with one another. Thus, depending on the functional disorders diagnosed, improved treatment outcomes may be obtained if a DPP IV inhibitor is combined with an active substance selected from among the other antidiabetic substances, especially active substances that lower the blood sugar level or the lipid level in the blood, raise the HDL level in the blood, lower blood pressure or are indicated in the treatment of atherosclerosis or obesity.

The dosage required of the DPP IV inhibitors when administered intravenously is 0.1 mg to 10 mg, preferably 0.25 mg to 5 mg, and when administered orally 0.5 mg to 100 mg, preferably 2.5 mg to 50 mg, in each case 1 to 4 times a day. For this purpose the compounds, optionally in combination with another active substance, may be formulated together with one or more inert conventional carriers and/or diluents, e.g. with maize starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propylene-glycol, cetylstearylalcohol, carboxymethylcellulose or fatty substances such as hard fat or suitable mixtures thereof, to form conventional galenic preparations such as tablets, coated tablets, capsules, powders, suspensions or suppositories.

The DPP IV inhibitors according to the invention are thus prepared by the skilled man using permitted formulation excipients as described in the prior art. Examples of such excipients are diluents, binders, carriers, fillers, lubricants, flow agents, crystallisation retardants, disintegrants, solubilisers, colourings, pH regulators, surfactants and emulsifiers.

Examples of suitable diluents include cellulose powder, calcium hydrogen phosphate, erythritol, (low-substituted) hydroxypropylcellulose, mannitol, pregelatinised starch or xylitol.

Examples of suitable binders include copolymers of vinylpyrrolidone with other vinyl derivatives (copovidone), hydroxypropylmethylcellulose (HPMC), hydroxypropylcellulose (HPC) polyvinylpyrrolidone (povidone), pregelatinised starch, or low-substituted hydroxypropylcellulose.

Examples of suitable lubricants include talc, polyethyleneglycol, calcium behenate, calcium stearate, hydrogenated castor oil or magnesium stearate.

Examples of suitable disintegrants include maize starch or crospovidone.

Suitable methods of preparing pharmaceutical formulations of the DPP IV inhibitors according to the invention are
  Direct tabletting of the active substance in powder mixtures with suitable tabletting excipients;
  Granulation with suitable excipients and subsequent mixing with suitable excipients and subsequent tabletting as well as film coating; or
  packing of powder mixtures or granules into capsules.

Suitable granulation methods are
  wet granulation in the intensive mixer followed by fluidised bed drying;
  one-pot granulation;
  fluidised bed granulation; or
  dry granulation (e.g. by roller compaction) with suitable excipients and subsequent tabletting or packing into capsules.

The DPP IV inhibitors mentioned above may also be used in conjunction with other active substances, by means of which improved treatment results can be obtained. Such a combined treatment may be given as a free combination of the substances or in the form of a fixed combination, for example in a tablet or capsule. Pharmaceutical formulations of the combination partner needed for this may either be obtained commercially as pharmaceutical compositions or may be formulated by the skilled man using conventional methods. The active substances which may be obtained commercially as pharmaceutical compositions are described in numerous places in the prior art, for example in the list of drugs that appears annually, the "Rote Liste®" of the federal association of the pharmaceutical industry, or in the annually updated compilation of manufacturers' information on prescription drugs known as the "Physicians' Desk Reference".

Examples of antidiabetic combination partners are metformin; sulphonylureas such as glibenclamide, tolbutamide, glimepiride, glipizide, gliquidon, glibornuride and gliclazide; nateglinide; repaglinide; thiazolidinediones such as rosiglitazone and pioglitazone; PPAR gamma modulators such as metaglidases; PPAR-gamma agonists such as GI 262570; PPAR-gamma antagonists; PPAR-gamma/alpha modulators such as tesaglitazar, muraglitazar and KRP297; PPAR-gamma/alpha/delta modulators; AMPK-activators such as AICAR; acetyl-CoA carboxylase (ACC1 and ACC2) inhibitors; diacylglycerol-acetyltransferase (DGAT) inhibitors; pancreatic beta cell GCRP agonists such as SMT3-receptor-agonists and GPR119; 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin zinc suspension and insulin glargin; Gastric inhibitory Peptide (GIP); pramlintide; amylin or GLP-1 and GLP-1 analogues such as Exendin-4; SGLT2-inhibitors such as KGT-1251; inhibitors of protein tyrosine-phosphatase; inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta 3 agonists such as ritobegron, YM 178, solabegron, talibegron, N-5984, GRC-1087, rafabegron, FMP825; aldosereductase inhibitors such as AS 3201, zenarestat, fidarestat, epalrestat, ranirestat, NZ-314, CP-744809, and CT-112; SGLT-1 or SGLT-2 inhibitors; KV 1.3 channel inhibitors; GPR40 modulators; SCD-1 inhibitors; CCR-2 antagonists; and other DPP IV inhibitors.

Examples of 11β-HSD1-inhibitors are described in
WO 2007/013929, WO 2007/007688, WO 2007/003521, WO 2006/138508, WO 2006/135795, WO 2006/135667, WO 2006/134481, WO 2006/134467, WO 2006/132436, WO 2006/132197, WO 2006/113261, WO 2006/106423, WO 2006/106052, WO 2006/105127, WO 2006/104280, WO 2006/100502, WO 2006/097337, WO 2006/095822, WO 2006/094633, WO 2006/080533, WO 2006/074330, WO 2006/074244, WO 2006/068992, WO 2006/068991, WO 2006/068199, WO 2006/066109, WO 2006/055752, WO 2006/053024, WO 2006/051662, WO 2006/050908, WO 2006/049952, WO 2006/048750, WO 2006/048331, WO 2006/048330, WO 2006/040329, WO 2006/037501, WO 2006/030805, WO 2006/030804, WO 2006/017542, WO 2006/024628, WO 2006/024627, WO 2006/020598, WO 2006/010546, WO 2006/002349, WO 2006/002350, WO 2006/012173, WO 2006/012227, WO 2006/012226, WO 2006/000371, WO 2005/118538, WO 2005/116002, WO 2005/110992, WO 2005/110980, WO 2005/108359, WO 2005/108361, WO 2005/108360, WO 2005/108368, WO 2005/103023, WO 2005/097764, WO 2005/097759, WO 2005/095350, WO 2005/075471, WO 2005/063247, WO 2005/060963, WO 2005/047250, WO 2005/046685, WO 2005/044192, WO 2005/042513, WO 2005/016877, WO 2004/113310, WO 2004/106294, WO 2004/103980, WO 2004/089896, WO 2004/089380, WO 2004/089471, WO 2004/089470, WO 2004/089367, WO 2005/073200, WO 2004/065351, WO 2004/058741, WO 2004/056745, WO 2004/056744, WO 2004/041264, WO 2004/037251, WO 2004/033427, WO 2004/011410, WO 2003/104208, WO 2003/104207, WO 2003/065983, WO 2003/059267, WO 2003/044009, WO 2003/044000, WO 2003/043999, WO 2002/076435, WO 2001/090094, WO 2001/090093, WO 2001/090092, WO 2001/090091, WO 2001/090090, US 2007/049632, US 2006/148871, US 2006/025445, US 2006/004049, US 2005/277647, US 2005/261302, US 2005/245534, US 2005/245532, US 2005/245533 and JP 2005/170939. The foregoing references are hereby incorporated by reference in their entireties. A representative example of an 11β-HSD1-inhibitor is the compound:

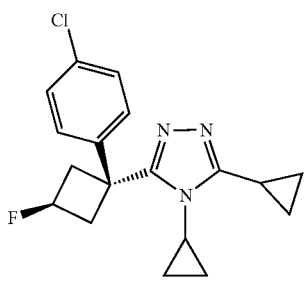 [SMILES: F[C@H]1C[C@](c2ccc(Cl)cc2)(c2nnc(C3CC3)n2C2CC2)C1]

and the salts thereof.

Examples of glycogen phosphorylase modulators are described in WO 2006/126695, WO 2006/082401, WO 2006/082400, WO 2006/059165, WO 2006/059164, WO 2006/059163, WO 2006/056815, WO 2006/055463, WO 2006/055462, WO 2006/055435, WO 2006/053274, WO 2006/052722, WO 2005/085245, WO 2005/085194, WO 2005/073231, WO 2005/073230, WO 2005/073229, WO 2005/067932, WO 2005/020987, WO 2005/020986, WO 2005/020985, WO 2005/019172, WO 2005/018637, WO 2005/013981, WO 2005/013975, WO 2005/012244, WO 2004/113345, WO 2004/104001, WO 2004/096768, WO 2004/092158, WO 2004/078743, WO 2004/072060, WO 2004/065356, WO 2004/041780, WO 2004/037233, WO 2004/033416, WO 2004/007455, WO 2004/007437, WO 2003/104188, WO 2003/091213, WO 2003/084923, WO 2003/084922, WO 2003/074532, WO 2003/074531, WO 2003/074517, WO 2003/074513, WO 2003/074485, WO 2003/074484, WO 2003/072570, WO 2003/059910, WO 2003/037864, WO 2002/096864, WO 2002/020530, WO 2001/094300, WO 2000/123347, WO 1996/39384, WO 1996/39385, EP 1391460, EP 1136071, EP 1125580, EP 1088824, EP 0978279, JP 2004196702, US 2004/002495, US 2003/195243, and U.S. Pat. No. 5,998,463. The foregoing references are hereby incorporated by reference in their entireties.

Examples of glucokinase-activators are described in WO 2007/017649, WO 2007/007910, WO 2007/007886, WO 2007/007042, WO 2007/007041, WO 2007/007040, WO 2007/006814, WO 2007/006761, WO 2007/006760, WO 2006/125972, WO 2006/125958, WO 2006/112549, WO 2006/059163, WO 2006/058923, WO 2006/049304, WO 2006/040529, WO 2006/040528, WO 2006/016194, WO 2006/016178, WO 2006/016174, WO 2005/121110, WO 2005/103021, WO 2005/095418, WO 2005/095417, WO 2005/090332, WO 2005/080360, WO 2005/080359, WO 2005/066145, WO 2005/063738, WO 2005/056530, WO 2005/054233, WO 2005/054200, WO 2005/049019, WO 2005/046139, WO 2005/045614, WO 2005/044801, WO 2004/081001, WO 2004/076420, WO 2004/072066, WO 2004/072031, WO 2004/063194, WO 2004/063179, WO 2004/052869, WO 2004/050645, WO 2004/031179, WO 2004/002481, WO 2003/095438, WO 2003/080585, WO 2003/055482, WO 2003/047626, WO 2003/015774, WO 2003/000267, WO 2003/000262, WO 2002/048106, WO 2002/046173, WO 2002/014312, WO 2002/008209, WO 2001/085707, WO 2001/085706, WO 2001/083478, WO 2001/083465, WO 2001/044216, and WO 2000/058293. The foregoing references are hereby incorporated by reference in their entireties.

Representative examples of glucokinase-activators are the compounds

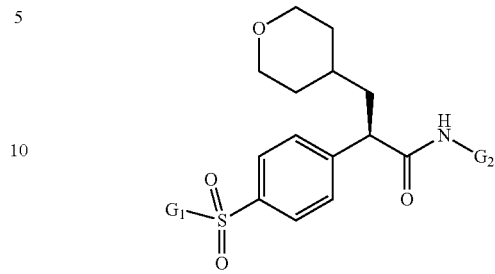

wherein $G_1$ denotes cyclopropyl or cyclobutyl and $G_2$ denotes 5-fluoro-thiazol-2-yl, 1-methyl-1H-pyrazol-3-yl, or pyrazin-2-yl; and

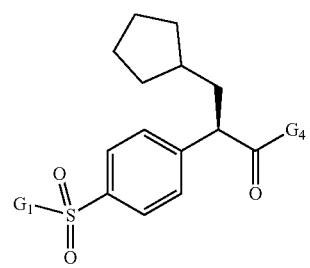

wherein $G_3$ denotes methyl or ethyl and $G_4$ denotes thiazol-2-yl, 4-methyl-thiazol-2-yl, 5-methyl-thiazol-2-yl, or pyrazin-2-yl and the salts thereof.

Examples of SGLT1 or SGLT2-inhibitors are described in WO 2006/108842, WO 2006/087997, WO 2006/080577, WO 2006/080421, WO 2006/073197, WO 2006/064033, WO 2006/062224, WO 2006/054629, WO 2006/037537, WO 2006/035796, WO 2006/018150, WO 2006/008038, WO 2006/002912, WO 2006/010557, WO 2006/011502, WO 2006/011469, WO 2005/121161, WO 2005/012326, WO 2005/095429, WO 2005/095372, WO 2005/095373, WO 2005/092877, WO 2005/085267, WO 2005/085265, WO 2005/085237, WO 2005/063785, WO 2005/021566, WO 2005/012243, WO 2005/012242, WO 2005/012326, WO 2005/012318, WO 2005/011592, WO 2004/113359, WO 2004/099230, WO 2004/089967, WO 2004/089966, WO 2004/087727, WO 2004/080990, WO 2004/058790, WO 2004/052903, WO 2004/052902, WO 2004/019958, WO 2004/018491, WO 2004/014932, WO 2004/014931, WO 2004/013118, WO 2003/099836, WO 2003/080635, WO 2003/020737, WO 2003/011880, WO 2003/000712, WO 2002/098893, WO 2002/088157, WO 2002/083066, WO 2002/068440, WO 2002/068439, WO 2002/064606, WO 2002/053573, WO 2002/044192, WO 2002/036602, WO 2002/028872, WO 2001/074835, WO 2001/074834, WO 2001/068660, WO 2001/027128, WO 2001/016147, JP 2005247834, JP 2004359630, JP 2004196788, JP 2003012686, and US 2006/063722. The foregoing references are hereby incorporated by reference in their entireties.

Representative examples of SGLT1 or SGLT2-inhibitors are the following compounds and the salts or complexes thereof with natural amino acids

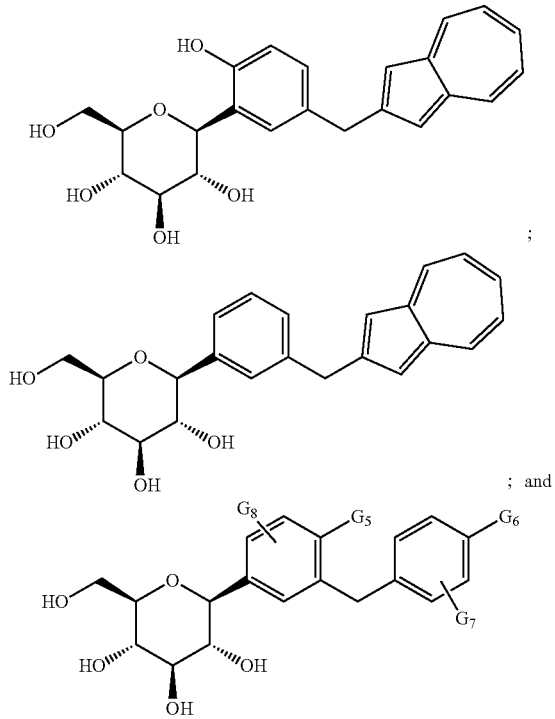

wherein $G_5$ and $G_8$ independently of one another denote hydrogen, fluorine, chlorine, bromine, cyano, methyl, ethyl, isopropyl, difluoromethyl, trifluoromethyl, ethynyl, prop-1-yn-1-yl, but-1-yn-1-yl, hydroxy, methoxy, ethoxy, difluoromethoxy, cyclopropyloxy, cyclobutyloxy, cyclopentyloxy or cyclohexyloxy; and $G_6$ denotes fluorine, chlorine, methyl, ethyl, methoxy, ethoxy, difluoromethoxy, trifluoromethoxy, trimethylsilylethyl, ethynyl, 2-hydroxyprop-2-ylethynyl, 2-methoxyprop-2-ylethynyl, 3-hydroxy-1-propyn-1-yl, 3-methoxy-1-propyn-1-yl, cyclopropyl, cyclobutyl, cyclopentyl, cyclohexyl, cyclopropyloxy, cyclobutyloxy, cyclopentyloxy, cyclohexyloxy, tetrahydrofuran-3-yloxy, tetrahydropyran-4-yloxy, piperidin-4-yloxy, N-methylpiperidin-4-yloxy and N-acetylpiperidin-4-yloxy; and $G_7$ denotes hydrogen or fluorine;

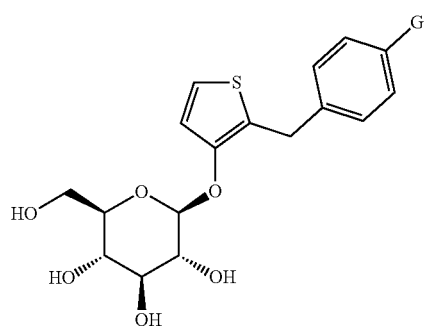

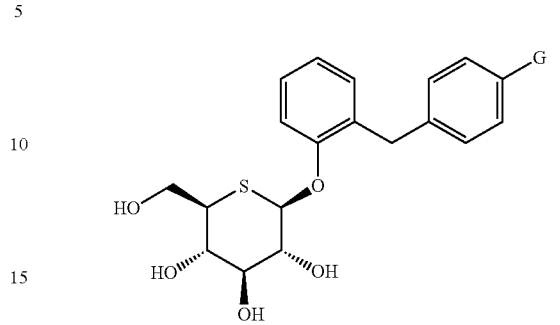

wherein G denotes fluorine, chlorine, methyl, ethyl, ethynyl, methoxy, ethoxy, difluoromethoxy, trifluoromethoxy, cyclobutyloxy, cyclopentyloxy, 3-tetrahydrofuranyloxy, or 4-tetrahydropyranyloxy;

wherein G denotes fluorine, chlorine, methyl, ethyl, ethynyl, methoxy, ethoxy, difluoromethoxy, trifluoromethoxy, cyclobutyloxy, cyclopentyloxy, 3-tetrahydrofuranyloxy, or 4-tetrahydropyranyloxy;

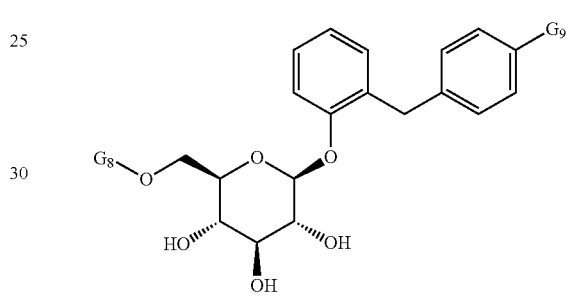

wherein $G_8$ denotes hydrogen, methoxycarbonyl, or ethoxycarbonyl and $G_9$ denotes fluorine, chlorine, methyl, ethyl, ethynyl, methoxy, ethoxy, difluoromethoxy, trifluoromethoxy, cyclobutyloxy, cyclopentyloxy, 3-tetrahydrofuranyloxy, or 4-tetrahydropyranyloxy; and

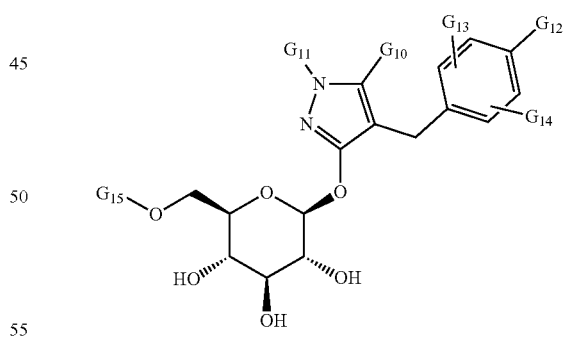

wherein:
$G_{10}$ denotes $C_{1-3}$-alkyl or perfluoro-$C_{1-3}$-alkyl;
$G_{11}$ denotes hydrogen, $C_{1-3}$-alkyl or perfluoro-$C_{1-3}$-alkyl;
$G_{12}$ denotes fluorine, chlorine, bromine, $C_{1-6}$-alkyl, $C_{1-6}$-alkyl substituted by 1 to 3 fluorine atoms, $C_{1-6}$-alkoxy, $C_{1-6}$-alkoxy substituted by 1 to 3 fluorine atoms, $C_{1-6}$-alkylthio, $C_{2-6}$-alkenyl, $C_{2-6}$-alkynyl, perfluoro-$C_{1-3}$-alkyl, cyclobutyloxy, cyclopentyloxy, cyclohexyloxy, tetrahydrofuranyloxy, or 4-tetrahydropyranyloxy; and
$G_{13}$ and $G_{14}$ independently of one another denote hydrogen, fluorine, chlorine, bromine, $C_{1-6}$-alkyl, $C_{1-6}$-alkyl substituted by 1 to 3 fluorine atoms, $C_{1-6}$-alkoxy, $C_{1-6}$-alkoxy substituted by 1 to 3 fluorine atoms, $C_{1-6}$-alkylthio, $C_{2-6}$-alkenyl, $C_{2-6}$-alkynyl, perfluoro-$C_{1-3}$-alkyl; and $G_{15}$ denotes hydrogen, $C_{2-20}$-alkanoyl, $C_{1-6}$-alkoxycarbonyl or benzoyl.

A particularly preferred example of an antidiabetic combination partner is metformin in doses of about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Another particularly preferred example is pioglitazone in a dosage of about 1-10 mg, 15 mg, 30 mg, or 45 mg once a day. Another particularly preferred example is miglitol in a dosage of about 10 mg to 50 mg or up to 100 mg 1-3 times a day.

Examples of combination partners that lower the lipid level in the blood are HMG-CoA-reductase inhibitors such as simvastatin, atorvastatin, lovastatin, fluvastatin, pravastatin and rosuvastatin; fibrates such as bezafibrate, fenofibrate, clofibrate, gemfibrozil, etofibrate and etofyllinclofibrate; nicotinic acid and the derivatives thereof such as acipimox; PPAR-alpha agonists; PPAR-delta agonists; inhibitors of acyl-coenzyme A:cholesterolacyltransferase (ACAT; EC 2.3.1.26) such as avasimibe; cholesterol resorption inhibitors such as ezetimib; substances that bind to bile acid, such as cholestyramine, colestipol and colesevelam; inhibitors of bile acid transport; HDL modulating active substances such as D4F, reverse D4F, LXR modulating active substances and FXR modulating active substances; CETP inhibitors such as torcetrapib, JTT-705 or compound 12 from WO 2007/005572; LDL receptor modulators; and ApoB100 antisense RNA. A particularly preferred example is atorvastatin in a dosage of about 1 mg to 40 mg or 10 mg to 80 mg once a day.

Examples of combination partners that lower blood pressure are beta-blockers such as atenolol, bisoprolol, celiprolol, metoprolol and carvedilol; diuretics such as hydrochlorothiazide, chlortalidon, xipamide, furosemide, piretanide, torasemide, spironolactone, eplerenone, amiloride and triamterene; calcium channel blockers such as amlodipine, nifedipine, nitrendipine, nisoldipine, nicardipine, felodipine, lacidipine, lercanipidine, manidipine, isradipine, nilvadipine, verapamil, gallopamil and diltiazem; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan and eprosartan. Particularly preferred examples are metoprolol in a dosage of 50 mg to 200 mg per day, Amlodipin in a dosage of 2.5 mg to 10 mg per day, ramipril in a dosage of 2.5 mg to 15 mg per day, valsartan in a dosage of 80 to 160 mg per day, and telmisartan in a dosage of 20 mg to 320 mg or 40 mg to 160 mg per day.

Examples of combination partners which increase the HDL level in the blood are Cholesteryl Ester Transfer Protein (CETP) inhibitors; inhibitors of endothelial lipase; regulators of ABC1; LXRalpha antagonists; LXRbeta agonists; PPAR-delta agonists; LXRalpha/beta regulators, and substances that increase the expression and/or plasma concentration of apolipoprotein A-I.

Examples of combination partners for the treatment of obesity are sibutramine; tetrahydrolipstatin (orlistat); alizyme; dexfenfluramine; axokine; cannabinoid receptor 1 antagonists such as the CB1 antagonist rimonobant; MCH-1 receptor antagonists; MC4 receptor agonists; NPY5 as well as NPY2 antagonists; beta3-AR agonists such as SB-418790 and AD-9677; 5HT2c receptor agonists such as APD 356; myostatin inhibitors; Acrp30 and adiponectin; steroyl CoA desaturase (SCD1) inhibitors; fatty acid synthase (FAS) inhibitors; CCK receptor agonists; Ghrelin receptor modulators; Pyy 3-36; orexin receptor antagonists; and tesofensine.

Examples of combination partners for the treatment of atherosclerosis are phospholipase A2 inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); oxLDL antibodies and oxLDL vaccines; apoA-1 Milano; ASA; and VCAM-1 inhibitors.

Examples of combination partners for the treatment of heart failure are beta-blockers such as atenolol, bisoprolol, celiprolol, and metoprolol; diuretics such as hydrochlorothiazide, chlortalidone, xipamide, furosemide, piretanide, torasemide, spironolactone, eplerenone, amiloride and triamterene; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan and eprosartan; heart glycosides such as digoxin and digitoxin; combined alpha/beta-blockers such as carvedilol; B-type natriuretic peptide (BNP) and BNP-derived peptides and BNP-fusion products. Particularly preferred examples are metoprolol in a dosage of 50 mg to 200 mg per day, ramipril in a dosage of 2.5 mg to 15 mg per day, valsartan in a dosage of 80 to 160 mg per day, telmisartan in a dosage of 20 mg to 320 mg or 40 mg to 160 mg per day, eplereron in a dosage of 25-100 mg, digoxin in a dosage of 0.25 mg to 0.6 mg per day carvedilol in a dosage of 3.25 mg to 100 mg, BNP (e.g. nesiritide) in a dosage of 2 µg/kg as a bolus followed by 0.01 µg/kg/min.

Drug combinations comprising the selected DPP IV inhibitors contain for example 1.75 mg to 10.5 mg glibenclamide, 500 mg to 3000 mg tolbutamide, 0.5-6 g glimepiride, 2.5 mg to 40 mg glipizide, 1-4×30 mg gliquidone, to 3×25 mg glibornuride, 80 mg to 160 mg gliclazide; 500 mg to 1000 mg, preferably 500 mg, 850 mg or 1000 mg metformin; 60 mg to 180 mg nateglinide; 0.25 mg to 4 mg repaglinide; 2 mg to 45 mg thiazolidinedione; 200 mg to 600 mg metaglidases; 2.5 mg to 5 mg PPAR gamma/alpha modulators; 0.1 mg to 100 mg alpha glucosidase blocker; 1-250 IU insulin; 15 µg to 120 µg Pramlintide; 5 mg to 80 mg statin; 50 mg to 1000 mg fibrate; 1000 mg to 3000 mg nicotinic acid or derivative; about 250 mg acipimox; about 10 mg of a cholesterol resorption inhibitor; 0.5 g to 30 g of a bile acid binding substance; 10 mg to 600 mg and preferably 10 mg to 120 mg CETP inhibitor; 2.5 mg to 100 mg beta-blocker; 3 mg to 200 mg diuretic; 2.5 mg to 500 mg calcium channel blocker; 1 mg to 40 mg ACE inhibitor; 5 mg to 600 mg angiotensin II receptor blocker; 10 mg to 15 mg sibutramine; about 120 mg orlistat; 15 mg to 30 mg dexfenfluramine; or 5 mg to 20 mg cannabinoid receptor antagonist, eplerenone in a dosage of 25 mg to 100 mg; digoxin in a dosage of 0.25 mg to 0.6 mg per day; carvedilol in a dosage of 3.25 mg to 100 mg; BNP (e.g. nesiritide) in a dosage of 2 µg/kg as a bolus followed by 0.01 µg/kg/min.

EXAMPLES

Example 1: Treatment of Pre-Diabetes

The efficacy of a DPPIV inhibitor according to the invention in the treatment of pre-diabetes characterised by pathological fasting glucose and/or impaired glucose tolerance can be tested using clinical studies. In studies over a shorter period (e.g. 2-4 weeks) the success of the treatment is examined by determining the fasting glucose values and/or the glucose values after a meal or after a loading test (oral glucose tolerance test or food tolerance test after a defined meal) after the end of the period of therapy for the study and comparing them with the values before the start of the study and/or with those of a placebo group. In addition, the fructosamine value can be determined before and after therapy and compared with the initial value and/or the placebo value. A significant drop in the fasting or non-fasting glucose levels demonstrates the efficacy of the treatment. In studies over a longer period (12 weeks or more) the success of the treatment is tested by determining the HbA1c value, by comparison with the initial value and/or with the value of the placebo group. A significant change in the HbA1c value compared with the initial value and/or the placebo value demonstrates the efficacy of the DPP IV inhibitor for treating pre-diabetes.

Example 2: Preventing Manifest Type 2 Diabetes

Treating patients with pathological fasting glucose and/or impaired glucose tolerance (pre-diabetes) is also in pursuit of the goal of preventing the transition to manifest type 2 diabetes. The efficacy of a treatment can be investigated in a comparative clinical study in which pre-diabetes patients are treated over a lengthy period (e.g. 1-5 years) with either an active substance or a combination of active substances or with placebo or with a non-drug therapy or other medicaments. During and at the end of the therapy, by determining the fasting glucose and/or a loading test (e.g. oGTT), a check is made to determine how many patients exhibit manifest type 2 diabetes, i.e. a fasting glucose level of >125 mg/dl and/or a 2 h value according to oGTT of >199 mg/dl. A significant reduction in the number of patients who exhibit manifest type 2 diabetes when treated with active substance or a combination of active substances as compared to one of the other forms of treatment, demonstrates the efficacy of the active substance or combination of active substances in preventing a transition from pre-diabetes to manifest diabetes.

Example 3: Treatment of Type 2 Diabetes

Treating patients with type 2 diabetes with the active substances according to the invention, in addition to producing an acute improvement in the glucose metabolic situation, prevents a deterioration in the metabolic situation in the long term. This can be observed is patients are treated for a longer period, e.g. 1-6 years, with the active substances or combinations of active substances according to the invention and are compared with patients who have been treated with other antidiabetic medicaments. There is evidence of therapeutic success compared with patients treated with other antidiabetic medicaments if no or only a slight increase in the fasting glucose and/or HbA1c value is observed. Further evidence of therapeutic success is obtained if a significantly smaller percentage of the patients treated with an active substance according to the invention or a combination of active substances according to the invention, compared with patients who have been treated with other medicaments, undergo a deterioration in the glucose metabolic position (e.g. an increase in the HbA1c value to >6.5% or >7%) to the point where treatment with an additional oral antidiabetic medicament or with insulin or with an insulin analogue or with another antidiabetic agent (e.g. GLP-1 analogue) is indicated.

Example 4: Treatment of Insulin Resistance

In clinical studies running for different lengths of time (e.g. 2 weeks to 12 months) the success of the treatment is checked using a hyperinsulinaemic euglycaemic glucose clamp study. A significant rise in the glucose infusion rate at the end of the study, compared with the initial value or compared with a placebo group, or a group given a different therapy, proves the efficacy of an active substance or combination of active substances in the treatment of insulin resistance.

Example 5: Treatment of Diabetic Hyper- or Dyslipidaemia

In clinical studies running for different lengths of time (e.g. 2 weeks to 60 months) on patients with type 2 diabetes the success of the treatment is checked by determining the total cholesterol, LDL-cholesterol, HDL-cholesterol, and plasma triglycerides. A significant fall in the total cholesterol, LDL-cholesterol, or plasma triglycerides and/or a rise in the HDL-cholesterol levels during or at the end of the study, compared with the initial value or compared with a placebo group, or a group given a different therapy, proves the efficacy of an active substance or combination of active substances in the treatment of diabetic dys- or hyperlipidaemia.

Example 6: Treatment of Hyperglycaemia

In clinical studies running for different lengths of time (e.g. 1 day to 24 months) the success of the treatment in patients with hyperglycaemia is checked by determining the fasting glucose or non-fasting glucose (e.g. after a meal or a loading test with oGTT or a defined meal). A significant fall in these glucose values during or at the end of the study, compared with the initial value or compared with a placebo group, or a group given a different therapy, proves the efficacy of an active substance or combination of active substances in the treatment of hyperglycaemia.

Example 7: Treatment of Gestational Diabetes

In clinical studies running for a shorter period (e.g. 2-4 weeks) the success of the treatment is checked by determining the fasting glucose values and/or the glucose values after a meal or after a loading test (oral glucose tolerance test or food tolerance test after a defined meal) at the end of the therapeutic period of the study and comparing them with the values before the start of the study and/or with those of a placebo group. In addition, the fructosamine value can be determined before and after treatment and compared with the initial value and/or a placebo value. A significant fall in the fasting or non-fasting glucose levels demonstrates the efficacy of an active substance or combination of active substances.

In longer-running studies (12 weeks or more) the success of the treatment is checked by determining the HbA1c value (compared with initial value and placebo group). A significant change in the HbA1c value compared with the starting value and/or placebo value demonstrates the efficacy of an active substance or combination of active substances in the treatment of gestational diabetes.

Example 8: Treatment of Women Who have had Gestational Diabetes

Patients with gestational diabetes have a significantly increased risk of contracting manifest type 2 diabetes after the pregnancy. Therapy may be provided with the objective of preventing the transition to manifest type 2. For this purpose, women with a history of gestational diabetes are treated either with an active substance according to the invention or a combination of active substances according to the invention or with placebo or with a non-drug therapy or with other medicaments, over a lengthy period (e.g. 1-4 years). During and at the end of the treatment a check is carried out by determining the fasting glucose and/or by a loading test (e.g. oGTT) to see how many patients have developed manifest type 2 diabetes (fasting glucose level >125 mg/dl and/or 2 h value after oGTT >199 mg/dl). A significant reduction in the number of patients who develop manifest type 2 diabetes when treated with an active substance according to the invention or a combination of active substances according to the invention, compared with a different type of therapy, is proof of the efficacy of an active substance or a combination of active substances in preventing manifest diabetes in women with a history of gestational diabetes.

Example 9: Prevention of Micro- or Macrovascular Complications

The treatment of type 2 diabetes or pre-diabetes patients with an active substance according to the invention or a combination of active substances according to the invention prevents or reduces microvascular complications (e.g. diabetic neuropathy, diabetic retinopathy, diabetic nephropathy, diabetic foot, diabetic ulcer) or macrovascular complications (e.g. myocardial infarct, acute coronary syndrome, unstable angina pectoris, stable angina pectoris, stroke, peripheral arterial occlusive disease, cardiomyopathy, heart failure, heart rhythm disorders, vascular restenosis). Type 2 diabetes or patients with pre-diabetes are treated long-term, e.g. for 1-6 years, with an active substance according to the invention or a combination of active substances according to the invention and compared with patients who have been treated with other antidiabetic medicaments or with placebo. Evidence of the therapeutic success compared with patients who have been treated with other antidiabetic medicaments or with placebo can be found in the smaller number of single or multiple complications. In the case of macrovascular events, diabetic foot and/or diabetic ulcer, the numbers are counted by anamnesis and various test methods. In the case of diabetic retinopathy the success of the treatment is determined by computer-controlled illumination and evaluation of the background to the eye or other ophthalmic methods. In the case of diabetic neuropathy, in addition to anamnesis and clinical examination, the nerve conduction rate can be measured using a calibrated tuning fork, for example. With regard to diabetic nephropathy the following parameters may be investigated before the start, during and at the end of the study: secretion of albumin, creatinin clearance, serum creatinin values, time taken for the serum creatinin values to double, time taken until dialysis becomes necessary.

Example 10: Treatment of Metabolic Syndrome

The efficacy of the active substances or combinations of active substances according to the invention can be tested in clinical studies with varying run times (e.g. 12 weeks to 6 years) by determining the fasting glucose or non-fasting glucose (e.g. after a meal or a loading test with oGTT or a defined meal) or the HbA1c value. A significant fall in these glucose values or HbA1c values during or at the end of the study, compared with the initial value or compared with a placebo group, or a group given a different therapy, proves the efficacy of an active substance or combination of active substances in the treatment of Metabolic Syndrome. Examples of this are a reduction in systolic and/or diastolic blood pressure, a lowering of the plasma triglycerides, a reduction in total or LDL cholesterol, an increase in HDL cholesterol or a reduction in weight, either compared with the starting value at the beginning of the study or in comparison with a group of patients treated with placebo or a different therapy.

Example 11: DPPIV Inhibitor Film-Coated Tablets

In order to prepare a granulating solution, copovidone is dissolved in purified water at ambient temperature. DPP IV inhibitor, mannitol, pre-gelatinised starch and maize starch are mixed in a suitable mixer in order to prepare a premix. The premix is moistened with the granulating solution and then granulated in a mixer with a high shear rate. The moist granules are screened through a screen with a mesh size of 1.6 mm. The granules are dried at about 60° C. in a fluidised bed dryer until a loss in drying value of 2-4% is obtained. The finished mixture is compressed to form tablet cores.

In a suitable mixer, hydroxypropylmethyl-cellulose, polyethyleneglycol, talc, titanium dioxide and iron oxide are suspended in purified water at ambient temperature to prepare a suspension for the tablet coating. The tablet cores are coated with this suspension until a weight increase of 3% is obtained. For example, the following tablet compositions may be obtained in this way:

| Ingredient | mg | mg | mg | mg | mg |
|---|---|---|---|---|---|
| DPP IV inhibitor | 0.500 | 1.000 | 2.500 | 5.000 | 10.000 |
| mannitol | 67.450 | 66.950 | 65.450 | 130.900 | 125.900 |
| pre-gelatinised starch | 9.000 | 9.000 | 9.000 | 18.000 | 18.000 |
| maize starch | 9.000 | 9.000 | 9.000 | 18.000 | 18.000 |
| copovidone | 2.700 | 2.700 | 2.700 | 5.400 | 5.400 |
| magnesium stearate | 1.350 | 1.350 | 1.350 | 2.700 | 2.700 |
| Total mass (tablet core) | 90.000 | 90.000 | 90.000 | 180.000 | 180.000 |
| HPMC | 1.500 | 1.500 | 1.500 | 2.500 | 2.500 |
| PEG | 0.150 | 0.150 | 0.150 | 0.250 | 0.250 |
| titanium dioxide | 0.750 | 0.750 | 0.750 | 1.250 | 1.250 |
| talc | 0.525 | 0.525 | 0.525 | 0.875 | 0.875 |
| iron oxide, yellow | 0.075 | 0.075 | 0.075 | 0.125 | 0.125 |
| Total mass (film-coated tablet) | 93.000 | 93.000 | 93.000 | 185.000 | 185.000 |

Example 12: Enhancing the Vitality and Secretion Capacity of Islets of Langerhans or Beta Cells This is done after successful isolation of the islets of Langerhans or pancreatic beta cells, by storing them, transporting them or cultivating them in a medium which contains DPP IV inhibitors in a concentration of 1 nmol/l to 1 µmol/l, preferably in a concentration of 1 nmol/l and 100 nmol/l, for future transplantation.

In addition, after transplantation with islets of Langerhans or pancreatic beta cells, the patients (and these may also be animals) are treated with DPP IV inhibitors in a daily dosage of between 1 mg and 200 mg, preferably with a dose of 5 mg and 100 mg of a DPP IV inhibitor, in order to enhance the vitality and secretion capacity of the transplant. This is tested either by analysis of the insulin secretion after stimulation with glucose or another agent that increases insulin secretion. Moreover, the improvement in the quality may also be checked in vitro or in animal models using the TUNEL technique, which is described in Diabetologia 42:566, 1999 or Diabetes 48:738, 1999 (investigation of apoptosis and inhibition thereof).

Example 13: Combined Treatment with DPP IV Inhibitor—Metformin

For treating type 2 diabetes or pre-diabetes a DPP IV inhibitor according to the invention may be combined with the anti-diabetically active substance metformin, either in a free combination or in a fixed combination in a tablet. A therapeutically effective dose of the DPP IV inhibitor (e.g. a dose of between 0.1 and 100 mg) may be combined with different doses of metformin, e.g. with 500 mg, 850 mg or 1000 mg metformin as a single dose with a total daily dose of metformin of 500-2850 mg, or with 500 mg, 1000 mg, 1500 mg, or 2000 mg metformin in delayed-release form. The clinical efficacy of such a combination with metformin can be tested in a clinical study. For this, patients with type 2 diabetes or with pre-diabetes are treated either with a DPP IV inhibitor on its own or with metformin on its own or with a combination von DPP IV inhibitor and metformin. The treatment lasts between 2 weeks and 6 years. Evidence that the combination is appropriate and effective can be found in the fact that the combination of a DPP-IV inhibitor with metformin leads to a significantly greater reduction in the fasting glucose and/or non-fasting glucose and/or the HbA1c value than either the DPP IV inhibitor alone or metformin alone.

Example 14: Combined Treatment with DPP IV Inhibitor—Glitazone

For treating type 2 diabetes or pre-diabetes a DPP IV inhibitor according to the invention may be combined with the anti-diabetically active substance group comprising the glitazones or thiazolidinediones (e.g. pioglitazone or rosiglitazone), either in a free combination or in a fixed combination in a tablet. A therapeutically effective dose of the DPP IV inhibitor (e.g. a dose of between 0.1 and 100 mg) may be combined with different doses of pioglitazone (15 mg, 30 mg, or 45 mg) or rosiglitazone (2 mg, 4 mg or 8 mg, given either once or twice a day). The clinical efficacy of such a combination with rosiglitazone or pioglitazone can be tested in a clinical study. For this, patients with type 2 diabetes or with pre-diabetes are treated either with a DPP IV inhibitor on its own or with rosiglitazone or pioglitazone alone or with a combination of DPP IV inhibitor and rosiglitazone or pioglitazone. The treatment lasts between 2 weeks and 6 years. Evidence that the combination is appropriate and effective can be found in the fact that the combination of a DPP-IV inhibitor with rosiglitazone or pioglitazone leads to a significantly greater reduction in the fasting glucose and/or non-fasting glucose and/or the HbA1c value than either the DPP IV inhibitor alone or rosiglitazone or pioglitazone alone.

Example 15: Combined Treatment with DPP IV Inhibitor—SGLT2 Inhibitor

For treating type 2 diabetes or pre-diabetes a DPP IV inhibitor according to the invention may be combined with the anti-diabetically active substance group comprising the SGLT-2 inhibitors, either in a free combination or in a fixed combination in a tablet. A therapeutically effective dose of the DPP IV inhibitor (e.g. a dose of between 0.1 and 100 mg) may be combined with different doses of SGLT-2 inhibitor (0.5 mg to 1000 mg). The clinical efficacy of such a combination with SGLT-2 inhibitor can be tested in a clinical study. For this, patients with type 2 diabetes or with pre-diabetes are treated either with a DPP IV inhibitor on its own or with a SGLT-2 inhibitor on its own or with a combination of DPP IV inhibitor and SGLT-2 inhibitor. The treatment lasts between 2 weeks and 6 years. Evidence that the combination is appropriate and effective can be found in the fact that the combination of a DPP-IV inhibitor with the SGLT-2 inhibitor leads to a significantly greater reduction in the fasting glucose and/or non-fasting glucose and/or the HbA1c value than either the DPP IV inhibitor alone or the SGLT-2 inhibitor alone.

Example 16: Combined Treatment with DPP IV Inhibitor—Antihypertensive

For treating a patient with type 2 diabetes or pre-diabetes or with Metabolic Syndrome a DPP IV inhibitor according to the invention may be combined with an anti-hypertensively active substance, either in a free combination or in a fixed combination in a tablet. A therapeutically effective dose of the DPP IV inhibitor (e.g. a dose of between 0.1 and 100 mg) may be combined with different doses of ACE-inhibitors (e.g. 2.5 mg to 15 mg ramipril), AT1-receptor-antagonists (e.g. 20 mg to 160 mg telmisartan), beta-blockers (e.g. 50 mg to 200 mg metoprolol), or diuretics (e.g. 12.5 mg to 25 mg hydrochlorothiazide). The clinical efficacy of such a combination with antihypertensives can be tested in a clinical study. For this, patients with type 2 diabetes or with pre-diabetes or with Metabolic Syndrome are treated either with a DPP IV inhibitor on its own or with an antihypertensive on its own or with a combination of DPP IV inhibitor and antihypertensive. The treatment lasts between 2 weeks and 6 years. Evidence that the combination is appropriate and effective can be found in the fact that the combination of a DPP-IV inhibitor with the antihypertensive lowers the fasting glucose and/or non-fasting glucose and/or the HbA1c value at least as much as the DPP IV inhibitor alone, and if the combination of the DPP-IV inhibitor with the antihypertensive lowers the systolic and/or diastolic arterial blood pressure at least as much as the antihypertensive alone.

Example 17: Combined Treatment with DPP IV Inhibitor—Lipid Lowering Agent

For treating a patient with type 2 diabetes or pre-diabetes or with Metabolic Syndrome or with diabetic dys- or hyperlipidaemia, a DPP IV inhibitor according to the invention may be combined with a lipid lowering agent/HDL-raising agent, either in a free combination or in a fixed combination in a tablet. A therapeutically effective dose of the DPP IV inhibitor (e.g. a dose of between 0.1 and 100 mg) may be combined with different doses of statins (e.g. 10 mg to 80 mg atorvastatin or 10 mg to 80 mg simvastatin), fibrates (e.g. fenofibrate), cholesterol absorption inhibitors, or with HDL-raising substances such as CETP-inhibitors (e.g. torcetrapib 10 mg to 120 mg once a day or 120 mg twice a day). The clinical efficacy of such a combination with lipid lowering agents/HDL-raising agents can be tested in a clinical study. For this, patients with type 2 diabetes or with pre-diabetes or with Metabolic Syndrome or with diabetic dys- or hyperlipidaemia are treated either with a DPP IV inhibitor on its own or with a lipid lowering agent/HDL-raising agent on its own or with a combination of DPP IV inhibitor and lipid lowering agent/HDL-raising agent. The treatment lasts between 2 weeks and 6 years. Evidence that the combination is appropriate and effective can be found in the fact that the combination of the DPP-IV inhibitor with the lipid lowering agent/HDL-raising agent lowers the fasting glucose and/or non-fasting glucose and/or the HbA1c value at least as much as the DPP IV inhibitor alone, and if the combination of the DPP-IV inhibitor with a lipid lowering agent/HDL-raising agent lowers the total cholesterol or LDL-cholesterol or plasma triglycerides at least as much or increases the HDL-cholesterol value at least as much as the lipid lowering agent/HDL-raising agent alone.

Example 18: Combined Treatment of DPP IV Inhibitor—BNP/BNP-Derived Peptides or BNP-Fusion Peptides in Patients with Heart Failure For treating a patient with acute heart failure, a DPP IV inhibitor according to the invention may be combined with a substance that favourably affects heart failure, either in a free combination or in a fixed combination in a tablet. A therapeutically effective dose of the DPP IV inhibitor (e.g. a dose of between 0.1 and 100 mg) may be combined with different doses of ACE-inhibitors (e.g. 2.5 mg to 15 mg ramipril), AT1-receptor-antagonists (e.g. 20 mg to 160 mg telmisartan), beta-blockers (e.g. 50 mg to 200 mg metoprolol), combined alpha/beta-blockers (e.g. 3.25 mg to 100 mg carvedilol), diuretics (e.g. 12.5 mg to 25 mg hydrochlorothiazide), mineralocorticoid receptor antagonists (e.g. 25 mg to 100 mg eplerenone; and/or B-type natriuretic peptide (BNP) (e.g. 2 µg/kg as a bolus followed by 0.01 µg/kg/min nesiritide), a BNP-derived peptide or a BNP-fusion product. The combination of BNP and DPP-IV inhibitor leads to a higher concentration of full length BNP (1-32) in vivo. The clinical efficacy of the combinations specified can be tested in clinical studies. The treatment lasts between 1 day and 6 years. Evidence that the combination is effective in treating acute heart failure can be found in the fact that compared with other therapies the combination leads to a significant improvement in the clinical situation (higher cardiac ejection output and/or reversal of pulmonary congestion, and/or reversal of pulmonary wedge pressure, and/or a reduction in mortality caused by acute heart failure).

Example 19: Treatment with DPP-IV Inhibitor in Patients with Heart Failure

A DPP IV inhibitor according to the invention may be used to treat a patient with chronic heart failure. This treatment leads to a higher concentration of endogenous full length BNP (1-32) in vivo. The clinical efficacy of this treatment is tested in clinical studies. The treatment lasts between 2 weeks and 6 years. Evidence that the combination is effective in treating chronic heart failure can be found in the fact that a DPP-IV inhibitor according to the invention leads to a significant improvement in the clinical situation compared with a different treatment or placebo (less frequent hospitalisation due to acute heart failure, the ability to walk longer distances, a higher loadability in ergometrics, a higher cardiac ejection output and/or reversal of pulmonary congestion, and/or a reduction in mortality caused by heart failure).

What is claimed is:

1. A method for the therapeutic treatment of a patient in whom pathological fasting glucose has been diagnosed, the method comprising the step of administering to the patient a medicament combination comprising:
   a DPP IV inhibitor of formula (I)

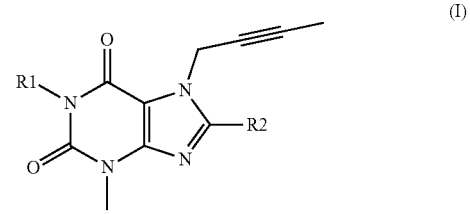

or one of the pharmaceutically acceptable salts thereof, wherein
   R1 denotes (4-methyl-quinazolin-2-yl)methyl, and
   R2 denotes 3-(R)-amino-piperidin-1-yl;
   and metformin.

2. The method according to claim 1, wherein
   the DPP IV inhibitor is 1-[(4-methyl-quinazolin-2-yl) methyl]-3-methyl-7-(2-butyn-1-yl)-8-(3-(R)-amino-piperidin-1-yl)-xanthin, or a pharmaceutically acceptable salt thereof.

3. The method according to claim 1, wherein the medicament combination comprises 2.5 mg or 5 mg of the DPP IV inhibitor.

4. The method according to claim 1, wherein the DPP IV inhibitor is administered orally in a total daily dose of 5 mg.

5. The method according to claim 1, wherein the medicament combination contains 500 mg to 1000 mg metformin.

6. The method according to claim 1, wherein the dose of metformin is 500 mg, 850 mg or 1000 mg metformin as a single dose with a total daily dose of metformin of 500-2850 mg, or with 500 mg, 1000 mg, 1500 mg, or 2000 mg metformin in delayed-release form.

7. The method according to claim 1, wherein the dose of metformin is 100 mg to 500 mg or 200 mg to 850 mg (1-3 times a day), or 300 mg to 1000 mg once or twice a day, or delayed-release metformin in a dose of 500 mg to 1000 mg once or twice a day or 500 mg to 2000 mg once a day.

8. The method according to claim 1, wherein the combination treatment of the DPP-IV inhibitor with metformin leads to a significantly greater reduction in the fasting glucose than either the DPP IV inhibitor alone or metformin alone.

9. The method according to claim 2, wherein the combination treatment of the DPP-IV inhibitor with metformin further leads to a significantly greater reduction in the HbA1c value than either the DPP IV inhibitor alone or metformin alone.

10. The method according to claim 8, wherein the combination treatment of the DPP-IV inhibitor with metformin further leads to a significantly greater reduction in the non-fasting glucose than either the DPP IV inhibitor alone or metformin alone.

11. The method according to claim 8, wherein the combination treatment of the DPP-IV inhibitor with metformin further leads to a significantly greater reduction in the non-fasting glucose and the HbA1c value than either the DPP IV inhibitor alone or metformin alone.

12. The method according to claim 1, wherein the medicament combination is a free combination.

13. The method according to claim 1, wherein the medicament combination is a fixed combination.

14. The method according to claim 1, wherein the medicament combination comprising the DPP IV inhibitor and metformin is administered as free or fixed combination, wherein the DPP IV inhibitor is 1-[(4-methyl-quinazolin-2-yl)methyl]-3-methyl-7-(2-butyn-1-yl)-8-(3-(R)-amino-piperidin-1-yl)-xanthin administered orally in a total daily dose of 5 mg.

15. The method according to claim 14, wherein the combination treatment of the DPP-IV inhibitor with metformin leads to a significantly greater reduction in the fasting glucose than either the DPP IV inhibitor alone or metformin alone.

16. The method according to claim 15, wherein the combination treatment of the DPP-IV inhibitor with metformin further leads to a significantly greater reduction in the HbA1c value than either the DPP IV inhibitor alone or metformin alone.

17. The method according to claim 14, wherein the total daily dose of metformin is 1000-2000 mg.

18. The method according to claim 15, wherein the total daily dose of metformin is 1000-2000 mg.

19. The method according to claim 16, wherein the total daily dose of metformin is 1000-2000 mg.

* * * * *

UNITED STATES PATENT AND TRADEMARK OFFICE
CERTIFICATE OF CORRECTION

Page 1 of 1

PATENT NO. : 12,171,767 B2
APPLICATION NO. : 17/681997
DATED : December 24, 2024
INVENTOR(S) : Klaus Dugi et al.

It is certified that error appears in the above-identified patent and that said Letters Patent is hereby corrected as shown below:

On the Title Page

In Column 1, after Item (22), add Item (30) and the following priority details:
-- (30) Foreign Application Priority Data
May 4, 2006 (EP) .......................... 206009203 --

Signed and Sealed this
Fourth Day of March, 2025

Coke Morgan Stewart
*Acting Director of the United States Patent and Trademark Office*